United States Patent
Armer et al.

(10) Patent No.: US 8,980,927 B2
(45) Date of Patent: *Mar. 17, 2015

(54) COMPOUNDS HAVING CRTH2 ANTAGONIST ACTIVITY

(71) Applicant: Atopix Therapeutics Limited, London (GB)

(72) Inventors: Richard Edward Armer, Oxon (GB); Eric Roy Pettipher, Oxon (GB); Mark Whittaker, Oxon (GB); Graham Michael Wynne, Oxon (GB); Julia Vile, Oxon (GB); Frank Schroer, Oxon (GB)

(73) Assignee: Atopix Therapeutics Limited, London (GB)

( * ) Notice: Subject to any disclaimer, the term of this patent is extended or adjusted under 35 U.S.C. 154(b) by 5 days.

This patent is subject to a terminal disclaimer.

(21) Appl. No.: 14/047,469

(22) Filed: Oct. 7, 2013

(65) Prior Publication Data
US 2014/0039012 A1    Feb. 6, 2014

Related U.S. Application Data

(60) Division of application No. 13/017,860, filed on Jan. 31, 2011, now Pat. No. 8,563,536, which is a continuation of application No. 12/828,800, filed on Jul. 1, 2010, now Pat. No. 7,919,512, which is a
(Continued)

(30) Foreign Application Priority Data

Jan. 18, 2008 (GB) .................................. 0800874.0
Nov. 10, 2008 (GB) .................................. 0820526.2

(51) Int. Cl.
    *A61K 31/44*      (2006.01)
    *A61K 31/4439*      (2006.01)
(Continued)

(52) U.S. Cl.
    CPC .......... *A61K 31/4439* (2013.01); *C07D 401/06* (2013.01); *A61K 45/06* (2013.01)
    USPC ....................................................... 514/339

(58) Field of Classification Search
None
See application file for complete search history.

(56) References Cited

U.S. PATENT DOCUMENTS

| | | | |
|---|---|---|---|
| 3,557,142 A | 1/1971 | Bell | |
| 3,843,683 A | 10/1974 | Bell | |

(Continued)

FOREIGN PATENT DOCUMENTS

| | | | |
|---|---|---|---|
| EP | 0 054 417 A1 | 6/1982 | |
| EP | 0 984 012 A2 | 3/2000 | |

(Continued)

OTHER PUBLICATIONS

Takeshita et al (Int Immunol 16:947-959, 2004).*

Armer, R.E., et al., "Indole-3-acetic acid antagonists of the prostaglandin $D_2$ receptor CRTH2," *J. Med. Chem.* 48:6174-6177, American Chemical Society, United States (2005).

Cross, P.E., et al., "Selective Thromboxane Synthetase Inhibitors. 2. 3-(1H-Imidazol-1-ylmethyl)-2-methyl-1H-indole-l-propanoic Acid and Analogues," *J. Med. Chem.* 29:342-345, American Chemical Society, United States (1986).

Abstract of Gillard, J.W., et al., "Indole 2-Propanoic Acids: The Medicinal Chemistry of L-665,240 a Potent, Non-Prostanoid Thromboxane Antagonist," Abstracts of Papers, ORGN-327, 195th ACS National Meeting, Toronto, Ontario, Canada, American Chemical Society, United States (1988).

(Continued)

*Primary Examiner* — Craig Ricci
(74) *Attorney, Agent, or Firm* — Sterne, Kessler, Goldstein & Fox P.L.L.C.

(57) ABSTRACT

Compounds of general formula (II)

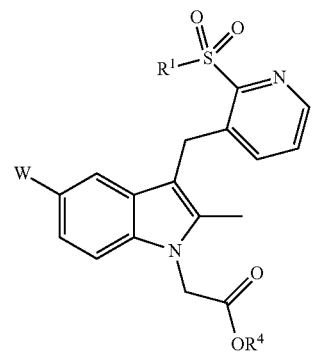

(II)

wherein
W is chloro or fluoro;
$R^1$ is phenyl optionally substituted with one or more substituents, selected from halo, —CN, —$C_1$-$C_6$ alkyl, —$SOR^3$, —$SO_2R^3$, —$SO_2N(R^2)_2$, —$N(R^2)_2$, —$NR^2C(O)R^3$, —$CO_2R^2$, —$CONR^2R^3$, —$NO_2$, —$OR^2$, —$SR^2$, —$O(CH_2)_pOR^2$, or —$O(CH_2)_pO(CH_2)_qOR^2$ wherein
each $R^2$ is independently hydrogen, —$C_1$-$C_6$ alkyl, —$C_3$-$C_8$ cycloalkyl, aryl or heteroaryl;
each $R^3$ is independently, —$C_1$-$C_6$ alkyl, —$C_3$-$C_8$ cycloalkyl, aryl or heteroaryl;
p and q are each independently an integer from 1 to 3; and
$R^4$ is hydrogen, $C_1$-$C_6$ alkyl, $C_1$-$C_6$ alkyl substituted with aryl, aryl, $(CH_2)_mOC(=O)C_1$-$C_6$alkyl, $((CH_2)_mO)_n$ $CH_2CH_2X$, $(CH_2)_mN(R^5)_2$ or $CH((CH_2)_mO(C=O)R^6)_2$;
m is 1 or 2;
n is 1-4;
X is $OR^5$ or $N(R^5)_2$;
$R^5$ is hydrogen or methyl; and
$R^6$ is $C_1$-$C_{18}$ alkyl;

and their pharmaceutically acceptable salts, hydrates, solvates, complexes or prodrugs are useful in orally administrable compositions for the treatment of allergic diseases such as asthma, allergic rhinitis and atopic dermatitis.

9 Claims, No Drawings

Related U.S. Application Data division of application No. 12/625,497, filed on Nov. 24, 2009, now Pat. No. 7,750,027, which is a continuation-in-part of application No. 12/356,822, filed on Jan. 21, 2009, now abandoned.

(51) Int. Cl.
*C07D 401/06* (2006.01)
*A61K 45/06* (2006.01)

(56) References Cited

U.S. PATENT DOCUMENTS

| | | | |
|---|---|---|---|
| 4,273,782 | A | 6/1981 | Cross et al. |
| 4,363,912 | A | 12/1982 | Cross et al. |
| 4,478,842 | A | 10/1984 | Renfroe |
| 4,774,240 | A | 9/1988 | Böshagen et al. |
| 4,859,692 | A | 8/1989 | Bernstein et al. |
| 5,214,059 | A | 5/1993 | Tegeler et al. |
| 5,410,061 | A | 4/1995 | Gilmore et al. |
| 5,496,844 | A | 3/1996 | Inai et al. |
| 5,532,237 | A | 7/1996 | Gallant et al. |
| 5,578,634 | A | 11/1996 | Bach et al. |
| 5,641,800 | A | 6/1997 | Bach et al. |
| 5,744,488 | A | 4/1998 | Cross et al. |
| 6,500,853 | B1 | 12/2002 | Seehra et al. |
| 6,521,659 | B2 | 2/2003 | Sredy et al. |
| 6,555,568 | B1 | 4/2003 | Sredy et al. |
| 6,602,890 | B2 | 8/2003 | Höfgen et al. |
| 6,730,794 | B2 | 5/2004 | Jones et al. |
| 6,797,708 | B2 | 9/2004 | McKew et al. |
| 6,828,344 | B1 | 12/2004 | Seehra et al. |
| 6,916,841 | B2 | 7/2005 | Seehra et al. |
| 6,995,263 | B2 | 2/2006 | Ackermann et al. |
| 7,166,607 | B2 | 1/2007 | Bonnert et al. |
| 7,321,001 | B2 | 1/2008 | Fu et al. |
| 7,348,351 | B2 | 3/2008 | Jennings et al. |
| 7,405,215 | B2 | 7/2008 | Bennani et al. |
| 7,534,897 | B2 | 5/2009 | Tanimoto et al. |
| 7,582,672 | B2 | 9/2009 | Middlemiss et al. |
| 7,601,749 | B2 | 10/2009 | Bennani et al. |
| 7,750,027 | B2 | 7/2010 | Armer et al. |
| 7,919,512 | B2 | 4/2011 | Armer et al. |
| 7,999,119 | B2 | 8/2011 | Armer et al. |
| 8,536,158 | B2 | 9/2013 | Armer et al. |
| 8,563,536 | B2 | 10/2013 | Armer et al. |
| 2001/0044437 | A1 | 11/2001 | Robinson et al. |
| 2005/0222201 | A1 | 10/2005 | Birkinshaw et al. |
| 2006/0111426 | A1 | 5/2006 | Bonnert et al. |
| 2006/0264444 | A1 | 11/2006 | Bonnert et al. |
| 2007/0232681 | A1 | 10/2007 | Middlemiss et al. |
| 2008/0027092 | A1 | 1/2008 | Bonnert et al. |
| 2008/0132574 | A1 | 6/2008 | Nakade et al. |
| 2008/0255100 | A1 | 10/2008 | Bennani et al. |
| 2008/0306109 | A1 | 12/2008 | Hynd et al. |
| 2009/0030014 | A1 | 1/2009 | Kugimiya et al. |
| 2009/0163518 | A1 | 6/2009 | Bonnert et al. |
| 2009/0170897 | A1 | 7/2009 | Corradini et al. |
| 2009/0186923 | A1 | 7/2009 | Armer et al. |
| 2009/0192195 | A1 | 7/2009 | Armer et al. |
| 2009/0286825 | A1 | 11/2009 | Wang |
| 2010/0004240 | A1 | 1/2010 | Giblin et al. |
| 2010/0016371 | A1 | 1/2010 | Giblin et al. |
| 2010/0016389 | A1 | 1/2010 | Bennani et al. |
| 2010/0022613 | A1 | 1/2010 | Armer et al. |
| 2010/0035956 | A1 | 2/2010 | Armer et al. |
| 2010/0041699 | A1 | 2/2010 | Boyd et al. |
| 2010/0056544 | A1 | 3/2010 | Lovell |
| 2010/0063103 | A1 | 3/2010 | Armer et al. |
| 2010/0266535 | A1 | 10/2010 | Armer et al. |
| 2011/0124683 | A1* | 5/2011 | Hunter et al. ............... 514/314 |

FOREIGN PATENT DOCUMENTS

| | | |
|---|---|---|
| GB | 1 356 834 | 7/1974 |
| GB | 2 422 829 A | 8/2006 |
| GB | 2 422 830 A | 8/2006 |
| GB | 2 422 831 A | 8/2006 |
| JP | 2001-247570 | 9/2001 |
| WO | WO 03/066047 A1 | 8/2003 |
| WO | WO 2005/040114 A1 | 5/2005 |
| WO | WO 2005/102388 A1 | 11/2005 |
| WO | WO 2005/121141 A1 | 12/2005 |
| WO | WO 2006/092579 A1 | 9/2006 |
| WO | WO 2006/095183 AI | 9/2006 |
| WO | WO 2007/010964 A1 | 1/2007 |
| WO | WO 2007/019675 A1 | 2/2007 |
| WO | WO 2007/107772 A1 | 9/2007 |
| WO | WO 2008/012511 A1 | 1/2008 |
| WO | WO 2009/037503 A2 | 3/2009 |
| WO | WO 2009/063202 A2 | 5/2009 |
| WO | WO 2009/063215 A2 | 5/2009 |
| WO | WO 2009/077728 A1 | 6/2009 |
| WO | WO 2009/090399 A1 | 7/2009 |
| WO | WO 2009/093026 A1 | 7/2009 |
| WO | WO 2010/008864 A2 | 1/2010 |

OTHER PUBLICATIONS

Johnson, M.G., et al., "Indole-phenylacetic acid inhibitors of CRTH2," Abstracts of Papers, MEDI-064, 235th ACS National Meeting, New Orleans, LA, American Chemical Society, United States (2008).

Kumar, S., et al., "Novel indium-mediated ternary reactions between indole-3-carboxaldehydes-allyl bromide-enamines: facile synthesis of bisindolyl- and indolyl-heterocylic alkanes," *Tetrahedron Letters* 44:2101-2104, Elsevier Science Ltd., England (2003).

Matassa, V.G., et al., "Evolution of a Series of Peptidoleukotriene Antagonists: Synthesis and Structure/Activity Relationships of 1,3,5-Substituted Indoles and Indazoles," *J. Med. Chem.* 33 :1781-1790, American Chemical Society, United States (1990).

Mathieson, J.M., et al., "Identification of Indole Derivatives Exclusively Interfering with a G Protein-Independent Signaling Pathway of the Prostaglandin D2 Receptor CRTH2," *Mol. Pharmacol.* 68:693-402, The American Society for Pharmacology and Experimental Therapeutics, United States (2005).

Royer, J.F., et al., "A novel antagonist of prostaglandin D2 blocks the locomotion of eosinophils and basophils," *Eur. J. Clin. Invest.* 38:663-671, Wiley-Blackwell, England (2008).

EMBASE, Accession No. 2005230213, Abstract of Werz, O. and Dieter, S., "Pharmacological intervention with 5-lipoxygenase: New insights and novel compounds," *Expert Opin. Ther. Pat.* 15:505-519, Informa Healthcare, England (2005).

Patent Abstracts of Japan, English language abstract of JP 2001-247570, (2001) (listed as document FP3 on accompanying form PTO/SB/08A).

Armer, R.E., et al., "Compounds having CRTH2 Antagonist Activity," U.S. Appl. No. 13/014,314, filed Jan. 26, 2011.

Office Action mailed Jun. 19, 2012, in U.S. Appl. No. 13/014,314, to Armer et al., filed Jan. 26, 2011.

Office Action mailed Jan. 9, 2013, in U.S. Appl. No. 13/014,314, to Armer et al., filed Jan. 26, 2011.

Notice of Allowance mailed May 8, 2013, in U.S. Appl. No. 13/014,314, to Armer et al., filed Jan. 26, 2011.

Han, Advances in Characterization of Pharmaceutical Hydrates, Trends in Bio/Pharmaceutical Industry, pp. 25-29 (Mar. 2006).

Stella, et al., "Prodrugs: Challenges and Rewards, Part 1" (2007).

Vippagunta, S.R., et al., "Crystalline solids," *Adv. Drug Deliv. Rev.* 48(1):3-26, Elsevier Science Publishers B.V., Netherlands (2001).

Williams, et al., *Foye's Principles of Medicinal Chemistry* 5th Edition, pp. 59-63 (2002).

* cited by examiner

COMPOUNDS HAVING CRTH2 ANTAGONIST ACTIVITY

The present invention relates to compounds which are useful as pharmaceuticals, to methods for preparing these compounds, compositions containing them and their use in the treatment and prevention of allergic diseases such as asthma, allergic rhinitis and atopic dermatitis and other inflammatory diseases mediated by prostaglandin $D_2$ ($PGD_2$) or other agonists acting at the CRTH2 receptor on cells including eosinophils, basophils and Th2 lymphocytes.

$PGD_2$ is an eicosanoid, a class of chemical mediator synthesised by cells in response to local tissue damage, normal stimuli or hormonal stimuli or via cellular activation pathways. Eicosanoids bind to specific cell surface receptors on a wide variety of tissues throughout the body and mediate various effects in these tissues. $PGD_2$ is known to be produced by mast cells, macrophages and Th2 lymphocytes and has been detected in high concentrations in the airways of asthmatic patients challenged with antigen (Murray et al., (1986), *N. Engl. J. Med.* 315: 800-804). Instillation of $PGD_2$ into airways can provoke many features of the asthmatic response including bronchoconstriction (Hardy et al., (1984) *N. Engl. J. Med.* 311: 209-213; Sampson et al., (1997) *Thorax* 52: 513-518) and eosinophil accumulation (Emery et al., (1989) *J. Appl. Physiol.* 67: 959-962).

The potential of exogenously applied $PGD_2$ to induce inflammatory responses has been confirmed by the use of transgenic mice overexpressing human $PGD_2$ synthase which exhibit exaggerated eosinophilic lung inflammation and Th2 cytokine production in response to antigen (Fujitani et al., (2002) *J. Immunol.* 168: 443-449).

The first receptor specific for $PGD_2$ to be discovered was the DP receptor which is linked to elevation of the intracellular levels of cAMP. However, $PGD_2$ is thought to mediate much of its proinflammatory activity through interaction with a G protein-coupled receptor termed CRTH2 (chemoattractant receptor-homologous molecule expressed on Th2 cells) which is expressed by Th2 lymphocytes, eosinophils and basophils (Hirai et al., (2001) *J. Exp. Med.* 193: 255-261, and EP0851030 and EP-A-1211513 and Bauer et al., EP-A-1170594). It seems clear that the effect of $PGD_2$ on the activation of Th2 lymphocytes and eosinophils is mediated through CRTH2 since the selective CRTH2 agonists 13,14 dihydro-15-keto-$PGD_2$ (DK-$PGD_2$) and 15R-methyl-$PGD_2$ can elicit this response and the effects of $PGD_2$ are blocked by an anti-CRTH2 antibody (Hirai et al., 2001; Monneret et al., (2003) *J. Pharmacol. Exp. Ther.* 304: 349-355). In contrast, the selective DP agonist BW245C does not promote migration of Th2 lymphocytes or eosinophils (Hirai et al., 2001; Gervais et al., (2001) *J. Allergy Clin. Immunol.* 108: 982-988). Based on this evidence, antagonising $PGD_2$ at the CRTH2 receptor is an attractive approach to treat the inflammatory component of Th2 dependent allergic diseases such as asthma, allergic rhinitis and atopic dermatitis.

EP-A-1170594 suggests that the method to which it relates can be used to identify compounds which are of use in the treatment of allergic asthma, atopic dermatitis, allergic rhinitis, autoimmune, reperfusion injury and a number of inflammatory conditions, all of which are mediated by the action of $PGD_2$ or other agonists at the CRTH2 receptor.

Compounds which bind to CRTH2 are taught in WO-A-03066046 and WO-A-03066047. These compounds are not new but were first disclosed, along with similar compounds, in GB 1356834, GB 1407658 and GB 1460348, where they were said to have anti-inflammatory, analgesic and antipyretic activity. WO-A-03066046 and WO-A-03066047 teach that the compounds to which they relate are modulators of CRTH2 receptor activity and are therefore of use in the treatment or prevention of obstructive airway diseases such as asthma, chronic obstructive pulmonary disease (COPD) and a number of other diseases including various conditions of bones and joints, skin and eyes, GI tract, central and peripheral nervous system and other tissues as well as allograft rejection. These compounds are all indole derivatives with an acetic acid substituent at the 3-position of the indole ring.

PL 65781 and JP 43-24418 also relate to indole-3 acetic acid derivatives which are similar in structure to indomethacin and, like indomethacin, are said to have anti-inflammatory and antipyretic activity. Thus, although this may not have been appreciated at the time when these documents were published, the compounds they describe are COX inhibitors, an activity which is quite different from that of the compounds of the present invention. Indeed, COX inhibitors are contraindicated in the treatment of many of the diseases and conditions, for example asthma and inflammatory bowel disease for which the compounds of the present invention are useful, although they may sometimes be used to treat arthritic conditions.

There is further prior art which relates to indole-1-acetic acid compounds, although these are not described as CRTH2 antagonists. For example WO-A-9950268, WO-A-0032180, WO-A-0151849 and WO-A-0164205 all relate to compounds which are indole-1-acetic acid derivatives but these compounds are said to be aldose reductase inhibitors useful in the treatment of diabetes mellitus (WO-A-9950268, WO-A-0032180 and WO-A-0164205) or hypouricemic agents (WO-A-0151849). There is no suggestion in any of these documents that the compounds would be useful for the treatment of diseases and conditions mediated by $PGD_2$ or other CRTH2 receptor agonists.

U.S. Pat. No. 4,363,912 relates to indole-1-alkyl carboxylic acid derivatives (including indole-1-acetic acid analogues) which are said to be inhibitors of thromboxane synthetase and to be useful in the treatment of conditions such as thrombosis, ischaemic heart disease and stroke. The compounds have an unsubstituted 3-pyridyl or 4-pyridyl substituent in an equivalent position to the pyridyl group of general formula (I). Evaluation of the closest analogue (5-fluoro-2-methyl-3-(pyridin-3-ylmethyl)-indol-1-yl)-acetic acid) that falls within the claims of U.S. Pat. No. 4,363,912 to the compounds of the present invention indicates that it is significantly less active as a CRTH2 antagonist than the compounds of the present invention. In contrast to the compounds of the present invention (which are all indole-1-acetic acid derivatives) the preferred compounds within U.S. Pat. No. 4,363,912 are 3-(indol-1-yl)-propionic acid derivatives.

WO-A-9603376 relates to compounds which are said to be $sPLA_2$ inhibitors which are useful in the treatment of bronchial asthma and allergic rhinitis. These compounds all have amide or hydrazide substituents in place of the carboxylic acid derivative of the compounds of the present invention.

JP 2001247570 relates to a method of producing a 3-benzothiazolylmethyl indole acetic acid, which is said to be an aldose reductase inhibitor.

U.S. Pat. No. 4,859,692 relates to compounds which are said to be leukotriene antagonists useful in the treatment of conditions such as asthma, hay fever and allergic rhinitis as well as certain inflammatory conditions such as bronchitis, atopic and ectopic eczema. Some of the compounds of this document are indole-1-acetic acids but the same authors, in *J. Med. Chem.*, 33, 1781-1790 (1990), teach that compounds with an acetic acid group on the indole nitrogen do not have significant peptidoleukotriene activity.

U.S. Pat. No. 4,273,782 is directed to indole-1-acetic acid derivatives which are said to be useful in the treatment of conditions such as thrombosis, ischaemic heart disease, stroke, transient ischaemic attack, migraine and the vascular complications of diabetes. There is no mention in the document of conditions mediated by the action of $PGD_2$ or other agonists at the CRTH2 receptor.

U.S. Pat. No. 3,557,142 relates to 3-substituted-1-indole carboxylic acids and esters which are said to be useful in the treatment of inflammatory conditions.

WO-A-03/097598 relates to compounds which are CRTH2 receptor antagonists. They do not have an aryl substituent at the indole-3 position.

Cross et al., *J. Med. Chem.* 29, 342-346 (1986) relates to a process for preparing indole-1-acetic acid derivatives from the corresponding esters. The compounds to which it relates are said to be inhibitors of thromboxane synthetase.

EP-A-0539117 relates to indole-1-acetic acid derivatives which are leukotriene antagonists.

US 2003/0153751 relates to indole-1-acetic acid derivatives which are $sPLA_2$ inhibitors. However, all of the exemplified compounds have bulky substituents at the 2- and 5-positions of the indole system and are therefore very different from the compounds of the present invention.

US 2004/011648 discloses indole-1-acetic acid derivatives which are inhibitors of PAI-1. There is no suggestion that the compounds might have CRTH2 antagonist activity.

WO 2004/058164 relates to compounds which are said to be asthma and allergic inflammation modulators. The only compounds for which activity is demonstrated are entirely different in structure from the indole-1-acetic acid derivatives of the present invention.

Compounds which bind to the CRTH2 receptor are disclosed in WO-A-03/097042 and WO-A-03/097598. These compounds are indole acetic acids but in WO-A-03/097042 the indole system is fused at the 2-3 positions to a 5-7 membered carbocyclic ring. In WO-A-03/097598 there is a pyrrolidine group at the indole 3-position.

WO-A-03/101981, WO-A-03/101961 and WO-A-2004/007451 all relate to indole-1-acetic acid derivatives which are said to be CRTH2 antagonists but which differ in structure from the compounds of general formula (I) because there is no spacer or an —S— or —$SO_2$— group attached to the indole 3-position in place of the $CH_2$ group of the compounds of the present invention as described below.

WO-A-2005/019171 also describes indole-1-acetic acid derivatives which are said to be CRTH2 antagonists and which are said to be useful for the treatment of various respiratory diseases. These compounds all have a substituent which is linked to the indole-3 position by an oxygen spacer.

WO-A-2005/094816 again describes indole-1-acetic acid compounds, this time with an aliphatic substituent at the 3-position of the indole ring. The compounds are said to be CRTH2 antagonists.

WO-A-2006/034419 relates to CRTH2 antagonist indole compounds which have a heterocyclic or heteroaryl substituent directly linked to the 3-position of the indole ring system.

In our earlier application, WO-A-2005/044260, we describe compounds which are antagonists of $PGD_2$ at the CRTH2 receptor. These compounds are indole-1-acetic acid derivatives substituted at the 3-position with a group $CR^8R^9$, wherein $R^9$ is hydrogen or alkyl and $R^8$ is an aryl group which may be substituted with one or more substituents. The compounds described in this document are potent antagonists in vitro of $PGD_2$ at the CRTH2 receptor. However, we have found that when tested in vivo, the pharmacokinetic profile of some compounds is not optimal and their potency in the whole blood eosinophil shape change test, which gives an indication of the likely in vivo activity of the compounds, is often somewhat less than might have been expected from the in vitro binding results.

In another of our earlier applications, WO2006/095183, the indole-1-acetic acid derivatives are substituted at the 3-position with a 1-benzenesulfonyl-1H-pyrrol-2-ylmethyl group, where the phenyl group of the benzenesulfonyl moiety may be substituted. These compounds are extremely active CRTH2 antagonists but are rapidly metabolised as determined by incubation with human microsome preparations.

Our application WO2008/012511 also relates to CRTH2 antagonist compounds, this time to indole-1-acetic acid derivatives substituted at the 3-position with a 2-phenylsulfonylbenzyl group. It was found that the position of the phenylsulfonyl substituent had a significant effect on both the activity of the compounds and their pharmacokinetic profile.

The present invention relate to pyridyl analogues of the compounds of WO2008/012511. These compounds do not suffer from the metabolic stability disadvantages of the compounds of WO2006/095183 and, surprisingly, it has been found that specific pyridyl regioisomers and substitution thereof gives rise to an optimal balance of potency and pharmacokinetic properties. Specifically it has been found that the introduction of a phenyl sulfonyl substituent onto the 2-position of the pyridin-3-yl regioisomer provides compounds with good potency in a functional in vitro assay together with good pharmacokinetics in vivo. That this combination should result in a highly beneficial combination of properties is not obvious and is not taught by the literature and patent applications relating to CRTH2 antagonists. It is particularly surprising that the 2-benzenesulfonyl-pyridin-3-yl compounds are potent and specific antagonists of the CRTH2 receptor both in a receptor binding assay and in a functional in vitro assay as we have found that the 3-benzenesulfonyl-pyridin-2-yl analogue is significantly less potent and that the 3-benzenesulfonyl-pyridin-4-yl analogue exhibits lower activity in the functional in vitro assay than might be expected from its receptor binding activity. It therefore appears that the position of the pyridyl nitrogen is particularly significant in the compounds of the invention.

The present invention therefore relates to novel compounds which bind to the CRTH2 receptor and which are therefore useful in the treatment of diseases and conditions mediated by the activity of $PGD_2$ at the CRTH2 receptor.

In the present invention there is provided a compound of general formula (I)

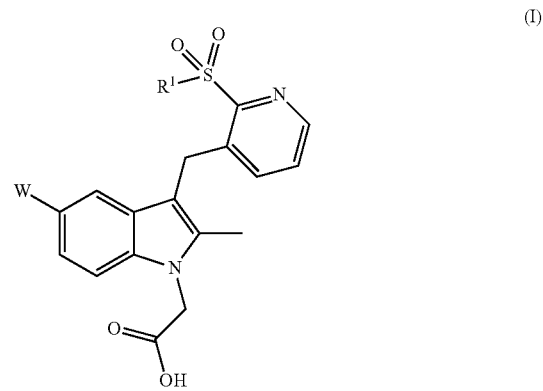

(I)

wherein
W is chloro or fluoro;

$R^1$ is phenyl optionally substituted with one or more substituents selected from halo, —CN, —$C_1$-$C_6$ alkyl, —$SOR^3$, —$SO_2R^3$, —$SO_2N(R^2)_2$, —$N(R)_2$, —$NR^2C(O)R^3$, —$CO_2R^2$, —$CONR^2R^3$, —$NO_2$, —$OR^2$, —$SR^2$, —$O(CH_2)_pOR^2$, and —$O(CH_2)_pO(CH_2)_qOR^2$ wherein
each $R^2$ is independently hydrogen, —$C_1$-$C_6$ alkyl, —$C_3$-$C_8$ cycloalkyl, aryl or heteroaryl;
each $R^3$ is independently, —$C_1$-$C_6$ alkyl, —$C_3$-$C_8$ cycloalkyl, aryl heteroaryl;
p and q are each independently an integer from 1 to 3;
or a pharmaceutically acceptable salt, hydrate, solvate, complex or prodrug thereof, The compounds of general formula (I) are antagonists at the CRTH2 receptor and are useful in the treatment of conditions which are mediated by $PGD_2$ or other agonists binding to CRTH2. These include allergic diseases, asthmatic conditions and inflammatory diseases, examples of which are asthma, including allergic asthma, bronchial asthma, exacerbations of asthma and related allergic diseases caused by viral infection, particularly those exacerbations caused by rhinovirus and respiratory syncytial virus intrinsic, extrinsic, exercise-induced, drug-induced and dust-induced asthma, treatment of cough, including chronic cough associated with inflammatory and secretory conditions of the airways and iatrogenic cough, acute and chronic rhinitis, including rhinitis medicamentosa, vasomotor rhinitis, perennial allergic rhinitis, seasonal allergic rhinitis, nasal polyposis, acute viral infection including common cold, infection due to respiratory syncytial virus, influenza, coronavirus and adenovirus, atopic dermatitis, contact hypersensitivity (including contact dermatitis), eczematous dermatitis, phyto dermatitis, photo dermatitis, sebhorroeic dermatitis, dermatitis herpetiformis, lichen planus, lichen sclerosis et atrophica, pyoderma gangrenosum, skin sarcoid, discoid lupus erythematosus, pemphigus, pemphigoid, epidermolysis bullosa urticaria, angioedema, vasculitides, toxic erythemas, cutaneous eosinophilias, alopecia greata, male-pattern baldness, Sweet's syndrome, Weber-Christian syndrome, erythema multiforme, cellulitis, panniculitis, cutaneous lymphomas, non-melanoma skin cancer and other dysplastic lesions; blepharitis conjunctivitis, especially allergic conjunctivitis, anterior and posterior uveitis, choroiditis, autoimmune, degenerative or inflammatory disorders affecting the retina, ophthalmitis; bronchitis, including infectious and eosinophilic bronchitis, emphysema, bronchiectasis, farmer's lung, hypersensitivity pneumonitis, idiopathic interstitial pneumonias, complications of lung transplantation, vasculitic and thrombotic disorders of the lung vasculature, pulmonary hypertension, food allergies, gingivitis, glossitis, periodontitis, oesophagitis including reflux, eosinophilic gastroenteritis, proctitis, pruris ani, celiac disease, food-related allergies, inflammatory bowel disease, ulcerative colitis and Crohn's disease, mastocytosis and also other CRTH2-mediated diseases, for example autoimmune diseases such as hyper IgE syndrome, Hashimoto's thyroiditis, Graves' disease, Addison's disease, diabetes mellitus, idiopathic thrombocytopaenic purpura, eosinophilic paschiitis, antiphospholipid syndrome and systemic lupus erythematosus, AIDS, leprosy, Sezary syndrome, paraneoplastic syndrome, mixed and undifferentiated connective tissue diseases, inflammatory myopathies including dermatomyositis and polymyositis, polymalgia rheumatica, juvenile arthritis, rheumatic fever, vasculitides including giant cell arteritis, Takayasu's arteritis, Churg-Strauss syndrome, polyarteritis nodosa, microscopic polyarteritis, temporal arteritis, myasthenia gravis, acute and chronic pain, neuropathic pain syndromes, central and peripheral nervous system complications of malignant, infectious or autoimmune processes, low back pain, familial Mediterranean Fever, Muckle-Wells syndrome, Familial Hibernian fever, Kikuchi disease, psoriasis, acne, multiple sclerosis, allograft rejection, reperfusion injury, chronic obstructive pulmonary disease, as well as rheumatoid arthritis, Still's disease, ankylosing spondylitis, reactive arthritis, undifferentiated spondarthropathy, psoriatic arthritis, septic arthritis and other infection-related arthopathies and bone disorders and osteoarthritis; acute and chronic crystal-induced synovitis including urate gout, calcium pyrophosphate deposition disease, calcium paptite related tendon syndrome and synovial inflammation, Behcet's disease, primary and secondary Sjogren's syndrome systemic sclerosis and limited scleroderma; hepatitis, cirrhosis of the liver, cholecystitis, pancreatitis, nephritis, nephritic syndrome, cystitis and Hunner's ulcer, acute and chronic urethritis, prostatitis, epididymitis, oophoritis, salpingitis, vulvo-vaginitis, Peyronie's disease, erectile dysfunction, Alzheimer's disease and other dementing disorders; pericarditis, myocarditis, inflammatory and auto-immune cardiomyopathies including myocardial sarcoid, ischaemic reperfusion injuries, endocarditis, valvulitis, aortitis, phlebitis, thrombosis, treatment of common cancers and fibrotic conditions such as idiopathic pulmonary fibrosis including cryptogenic fibrosing alveolitis, keloids, excessive fibrotic scarring/adhesions post surgery, liver fibrosis including that associated with hepatitis B and C, uterine fibroids, sarcoidosis, including neurosarcoidosis, sclerodeana, kidney fibrosis resulting from diabetes, fibrosis associated with RA, atherosclerosis, including cerebral atherosclerosis, vasculitis, myocardial fibrosis resulting from myocardial infarction, cystic fibrosis, restenosis, systemic sclerosis, Dupuytren's disease, fibrosis complicating anti-neoplastic therapy and chronic infection including tuberculosis and aspergillosis and other fungal infections, CNS fibrosis following stroke or the promotion of healing without fibrotic scarring.

The improved potency in the whole blood eosinophil shape change test and pharmacokinetic profile of the compounds of general formula (I) is particularly surprising since some of the compounds of WO-A-2005/044260, which are closest in structure to the compounds of general formula (I) do not have these advantageous properties. In particular, the compound of Example 17 of WO-A-2005/044260 is similar to the compounds of the present invention and might have been expected to have similar properties. However, in in vivo experiments carried out in the dog, the replacement of the 4-methylsulfonylbenzyl group in Example 17 of WO-A-2005/044260 with the 2-(benzenesulfonyl)pyridine-3-ylmethyl group in the compounds of formula (I) has a significant effect on the pharmacokinetics of the compounds because when Compound 17 of WO-A-2005/044260 is administered orally, its pharmacokinetic profile in vivo is less favourable than that of the compounds of general formula (I).

In addition for many of the compounds of WO-A-2005/044260, we have found that their in vitro whole blood eosinophil shape change activity is often less than might have been expected from their in vitro activity as measured by radioligand binding experiments to the CRTH2 receptor.

Furthermore, the improvement in activity is very specific to the group of compounds of general formula (I). Compounds which are even more closely related to the compounds specifically disclosed in WO-A-2005/044260 do not have such favourable properties. For example, the analogues of general formula (I) in which the $SO_2R$ group is not at a position on the pyridine ring adjacent the linking methylene moiety which is joined to the 3-position of the indolyl scaffold are less active in in vitro whole blood eosinophil shape change tests.

In the present specification "$C_1$-$C_6$ alkyl" refers to a straight or branched saturated hydrocarbon chain having one to six carbon atoms and optionally substituted with one or more halo substituents and/or with one or more $C_3$-$C_8$ cycloalkyl groups. Examples include methyl, ethyl, n-propyl, isopropyl, t-butyl, n-hexyl, trifluoromethyl, 2-chloroethyl, methylenecyclopropyl, methylenecyclobutyl, methylenecyclobutyl and methylenecyclopentyl.

The term "$C_1$-$C_{18}$ alkyl" has a similar meaning to the above except that it refers to a straight or branched saturated hydrocarbon chain having one to eighteen carbon atoms.

In the present specification "$C_3$-$C_8$ cycloalkyl" refers to a saturated carbocyclic group having three to eight ring atoms and optionally substituted with one or more halo substituents. Examples include cyclopropyl, cyclopentyl, cyclohexyl and 4-fluorocyclohexyl.

In the present specification, "halo" refers to fluoro, chloro, bromo or iodo.

The term "aryl" in the context of the present specification refer to a ring system with aromatic character having from 5 to 14 ring carbon atoms and containing up to three rings. Where an aryl group contains more than one ring, not all rings must be fully aromatic in character. Examples of aromatic moieties are benzene, naphthalene, indane and indene.

The term "heteroaryl" in the context of the specification refer to a ring system with aromatic character having from 5 to 14 ring atoms, at least one of which is a heteroatom selected from N, O and S, and containing up to three rings. Where a heteroaryl group contains more than one ring, not all rings must be fully aromatic in character. Examples of heteroaryl groups include pyridine, pyrimidine, indole, benzofuran, benzimidazole and indolene.

General formula (I) as shown above is intended to include all isotopic variants, for example the hydrogen atoms of the molecule can be $^1H$, $^2H$ or $^3H$ and the carbon atoms can be $^{12}C$ or $^{14}C$.

Appropriate pharmaceutically and veterinarily acceptable salts of the compounds of general formulae (I) include basic addition salts such as sodium, potassium, calcium, aluminium, zinc, magnesium and other metal salts as well as choline, diethanolamine, ethanolamine, ethyl diamine, megulmine and other well known basic addition salts as summarised in Paulekuhn et al., (2007) *J. Med. Chem.* 50: 6665-6672 and/or known to those skilled in the art.

Salts which are not pharmaceutically or veterinarily acceptable may still be valuable as intermediates.

Prodrugs are any covalently bonded compounds which release the active parent drug according to general formula (I) in vivo. Examples of prodrugs include alkyl esters of the compounds of general formula (I), for example the esters of general formula (II) below.

In particularly suitable compounds of general formula (I), W is a fluoro substituent and the phenyl group $R^1$ is unsubstituted or is substituted with a single halo substituent, usually fluoro or chloro, which is generally at the 4-position of the phenyl group $R^1$.

Particularly active compounds of the present invention are:
(3-{[2-(Benzenesulfonyl)pyridin-3-yl]methyl}-5-fluoro-2-methylindol-1-yl)-acetic acid;
[5-Fluoro-3-({2-[(4-fluorobenzene)sulfonyl]pyridin-3-yl}methyl)-2-methylindol-1-yl]-acetic acid;
[3-({2-[(47Chlorobenzene)sulfonyl]pyridin-3-yl}methyl)-5-fluoro-2-methylindol-1-yl]-acetic acid;
or the $C_1$-$C_6$ alkyl, aryl, $(CH_2)_mOC(=O)C_1$-$C_6$alkyl, $((CH_2)_mO)_nCH_2CH_2X$, $(CH_2)_mN(R^5)_2$ or $CH((CH_2)_mO(C=O)R^6)_2$ ester thereof;
m is 1 or 2;
n is 1-4;
X is $OR^5$ or $N(R^5)_2$;
$R^5$ is hydrogen or methyl;
$R^6$ is $C_1$-$C_{18}$ alkyl.

In a further aspect of the present invention, there is provided a compound of general formula (II):

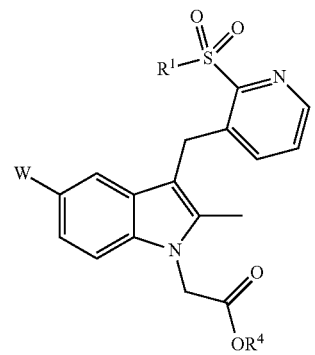

II wherein W and $R^1$ are as defined for general formula (I); and
$R^4$ is $C_1$-$C_6$ alkyl, $C_1$-$C_6$ alkyl substituted with aryl, aryl, $(CH_2)_mOC(=O)C_1$-$C_6$alkyl, $((CH_2)_mO)_nCH_2C_2X$, $(CH_2)_mN(R^5)_2$ or $CH((CH_2)_mO(C=O)R^6)_2$;
m is 1 or 2;
n is 1-4;
X is $OR^5$ or $N(R^5)_2$;
$R^5$ is hydrogen or methyl;
$R^6$ is $C_1$-$C_{18}$ alkyl;
or a pharmaceutically acceptable salt, hydrate, solvate, complex or prodrug thereof.

Compounds of general formula (II) are novel and may be used as prodrugs for compounds of general formula (I). When the compound of general formula (II) acts as a prodrug, it is later transformed to the drug by the action of an esterase in the blood or in a tissue of the patient.

Examples of particularly suitable $R^4$ groups when the compound of general formula (II) is used as a prodrug include methyl, ethyl, propyl, phenyl, $-O(CH_2)_2O(CH_2)_2OR^5$, $-O(CH_2)_2O(CH_2)_2O(CH_2)_2OR^5$, $-O(CH_2)_2O(CH_2)_2NR^5{}_2$, $-O(CH_2)_2O(CH_2)_2O(CH_2)_2NR^5{}_2$, $-CH_2OC(=O)$tBu, $-CH_2CH_2N(Me)_2$, $-CH_2CH_2NH_2$ or $-CH(CH_2O(C=O)R^6)_2$ wherein $R^5$ and $R^6$ are as defined above.

In addition to their use as prodrugs, compounds of formula (II) wherein $R^4$ is $C_1$-$C_6$ alkyl or benzyl may be used in a process for the preparation of a compound of general formula (I), the process comprising reacting the compound of general formula (II) with a base such as sodium hydroxide or lithium hydroxide. The reaction may take place in an aqueous solvent or an organic solvent or a mixture of the two. A typical solvent used for the reaction is a mixture of tetrahydrofuran and water.

Compounds of general formula (II) may be prepared from compounds of general formula (III):

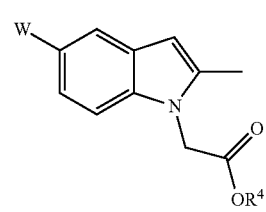

III wherein W is as defined in general formula (I) and $R^4$ is as defined in general formula (II); by reaction with an aldehyde of general formula (IV):

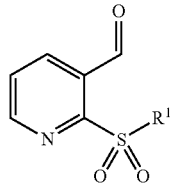

(IV)

wherein $R^1$ is as defined for general formula (I). The reaction may be carried out in the presence of trimethylsilyltriflate (TMSOTf) in a non polar organic solvent and at reduced temperature, for example −5 to 10° C., typically 0° C. The intermediate product is then reduced, for example with a trialkylsilane such as triethylsilane.

Procedures for the preparation of compounds of general formula (III) are known to those skilled in the art and in general involve alkylation of the 5-halo-indole derivative at the 1-position with an alpha-bromoacetate derivative or related alkylating agent. 5-Halo-indole derivatives are readily available or may be prepared by known methods.

Compounds of general formula (IV) may be prepared by the reaction of a compound of general formula (V):

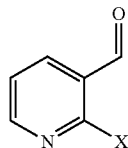

(V)

wherein X is a leaving group such as halo, especially fluoro or chloro;
with a compound of general formula (VI):

$R^1$—SO$_2$Na     (VI)

wherein $R^1$ is as defined for general formula (I).

The reaction may be carried out in a polar organic solvent such as DMSO at elevated temperature, typically reflux temperature for a prolonged period, for example 48 to 120 hours.

Compounds of general formula (V) and (VI) are commercially available.

Compounds of general formula (I) are CRTH2 receptor antagonists and compounds of general formula (II) are pro-drugs for compounds of general formula (I). Compounds of general formulae (I) and (II) are therefore useful in a method for the treatment of diseases and conditions mediated by PGD$_2$ or other agonists at the CRTH2 receptor, the method comprising administering to a patient in need of such treatment a suitable amount of a compound of general formula (I) or (II).

In a third aspect of the invention, there is provided a compound of general formula (I) or (II) for use in medicine, particularly for use in the treatment or prevention of diseases and conditions mediated by PGD$_2$ or other CRTH2 receptor agonists.

Furthermore, there is also provided the use of a compound of general formula (I) or (II) in the preparation of an agent for the treatment or prevention of diseases and conditions mediated by CRTH2 receptor agonists, particularly PGD$_2$.

As mentioned above, such diseases and conditions include allergic diseases, asthmatic conditions and inflammatory diseases, examples of which are asthma, including allergic asthma, bronchial asthma, intrinsic, extrinsic, exercise-induced, drug-induced and dust-induced asthma, treatment of cough, including chronic cough associated with inflammatory and secretory conditions of the airways and iatrogenic cough, acute and chronic rhinitis, including rhinitis medicamentosa, vasomotor rhinitis, perennial allergic rhinitis, seasonal allergic rhinitis, nasal polyposis, acute viral infection including common cold, infection due to respiratory syncytial virus, influenza, coronavirus and adenovirus, atopic dermatitis, contact hypersensitivity (including contact dermatitis), eczematous dermatitis, phyto dermatitis, photo dermatitis, sebhorroeic dermatitis, dermatitis herpetiformis, lichen planus, lichen sclerosis et atrophica, pyoderma gangrenosum, skin sarcoid, discoid lupus erythematosus, pemphigus, pemphigoid, epidermolysis bullosa urticaria, angioedema, vasculitides, toxic erythemas, cutaneous eosinophilias, alopecia greata, male-pattern baldness, Sweet's syndrome, Weber-Christian syndrome, erythema multiforme, cellulitis, panniculitis, cutaneous lymphomas, non-melanoma skin cancer and other dysplastic lesions; blepharitis conjunctivitis, especially allergic conjunctivitis, anterior and posterior uveitis, choroiditis, autoimmune, degenerative or inflammatory disorders affecting the retina, ophthalmitis; bronchitis, including infectious and eosinophilic bronchitis, emphysema, bronchiectasis, farmer's lung, hypersensitivity pneumonitis, idiopathic interstitial pneumonias, complications of lung transplantation, vasculitic and thrombotic disorders of the lung vasculature, pulmonary hypertension, food allergies, gingivitis, glossitis, periodontitis, oesophagitis including reflux, eosinophilic gastroenteritis, proctitis, pruris ani, celiac disease, food-related allergies, inflammatory bowel disease, ulcerative colitis and Crohn's disease, mastocytosis and also other CRTH2-mediated diseases, for example autoimmune diseases such as hyper IgE syndrome, Hashimoto's thyroiditis, Graves' disease, Addison's disease, diabetes mellitus, idiopathic thrombocytopaenic purpura, eosinophilic paschiitis, antiphospholipid syndrome and systemic lupus erythematosus, AIDS, leprosy, Sezary syndrome, paraneoplastic syndrome, mixed and undifferentiated connective tissue diseases, inflammatory myopathies including dermatomyositis and polymyositis, polymyalgia rheumatica, juvenile arthritis, rheumatic fever, vasculitides including giant cell arteritis, Takayasu's arteritis, Churg-Strauss syndrome, polyarteritis nodosa, microscopic polyarteritis, temporal arteritis, myasthenia gravis, acute and chronic pain, neuropathic pain syndromes, central and peripheral nervous system complications of malignant, infectious or autoimmune processes, low back pain, familial Mediterranean Fever, Muckle-Wells syndrome, Familial Hibernian fever, Kikuchi disease, psoriasis, acne, multiple sclerosis, allograft rejection, reperfusion injury, chronic obstructive pulmonary disease, as well as rheumatoid arthritis, Still's disease, ankylosing spondylitis, reactive arthritis, undifferentiated spondarthropathy, psoriatic arthritis, septic arthritis and other infection-related arthopathies and bone disorders and osteoarthritis; acute and chronic crystal-induced synovitis including urate gout, calcium pyrophosphate deposition disease, calcium paptite related tendon syndrome and synovial inflammation, Behcet's disease, primary and secondary Sjogren's syndrome systemic sclerosis and limited scleroderma; hepatitis, cirrhosis of the liver, cholecystitis, pancreatitis, nephritis, nephritic syndrome, cystitis and Runner's ulcer, acute and chronic urethritis, prostatitis, epididymitis, oophoritis, salpingitis, vulvo-vaginitis, Peyronie's disease, erectile dysfunction, Alzheimer's disease and other dementing disorders; pericarditis, myocarditis, inflammatory and auto-immune cardiomyopathies including myocardial sarcoid, ischaemic reperfusion injuries, endocarditis, valvulitis, aortitis, phlebitis, thrombosis, treatment of common cancers and fibrotic conditions such as idiopathic pulmonary fibrosis including cryptogenic fibrosing alveolitis, keloids, excessive fibrotic scarring/adhesions post surgery, liver fibrosis including that associated with hepatitis B and C, uterine fibroids, sarcoidosis, including neurosarcoidosis, scleroderma, kidney fibrosis resulting from diabetes, fibrosis associated with RA, atherosclerosis, including cerebral atherosclerosis, vasculitis, myocardial fibrosis resulting from myocardial infarction, cystic fibrosis, restenosis, systemic sclerosis, Dupuytren's disease, fibrosis complicating anti-neoplastic therapy and chronic infection including tuberculosis and aspergillosis and other fungal infections, and CNS fibrosis following stroke. The compounds are also of use in the promotion of healing without fibrotic scarring.

The compounds are particularly effective when used for the treatment or prevention of allergic asthma, perennial allergic rhinitis, seasonal allergic rhinitis, atopic dermatitis, contact hypersensitivity (including contact dermatitis), conjunctivitis, especially allergic conjunctivitis, vernal keratoconjunctivitis and atopic keratoconjunctivitis, eosinophilic bronchitis, food allergies, eosinophilic gastroenteritis, inflammatory bowel disease, ulcerative colitis and Crohn's disease, mastocytosis and also other PGD2-mediated diseases, for example autoimmune diseases such as hyper IgE syndrome and systemic lupus erythematus, psoriasis, acne, multiple sclerosis, allograft rejection, reperfusion injury, chronic obstructive pulmonary disease, as well as rheumatoid arthritis, psoriatic arthritis, osteoarthritis and fibrotic diseases caused/exacerbated by Th2 immune responses, for example idiopathic pulmonary fibrosis and hypertrophic scars, The compounds of general formula (I) or (II) must be formulated in an appropriate manner depending upon the diseases or conditions they are required to treat.

Therefore, in a further aspect of the invention there is provided a pharmaceutical composition comprising a compound of general formula (I) or (II) together with a pharmaceutical excipient or carrier. Other active materials may also be present, as may be considered appropriate or advisable for the disease or condition being treated or prevented.

The carrier, or, if more than one be present, each of the carriers, must be acceptable in the sense of being compatible with the other ingredients of the formulation and not deleterious to the recipient.

The formulations include those suitable for oral, rectal, nasal, bronchial (inhaled), topical (including eye drops, buccal and sublingual), vaginal or parenteral (including subcutaneous, intramuscular, intravenous and intradermal) administration and may be prepared by any methods well known in the art of pharmacy.

The route of administration will depend upon the condition to be treated but preferred compositions are formulated for oral, nasal, bronchial or topical administration.

The composition may be prepared by bringing into association the above defined active agent with the carrier, in general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of general formula (I) or (ii) in conjunction or association with a pharmaceutically or veterinarily acceptable earner or vehicle.

Formulations for oral administration in the present invention may be presented as: discrete units such as capsules, sachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate, stearic acid, silicone fluid, talc waxes, oils and colloidal silica. Flavouring agents such as peppermint, oil of wintergreen, cherry flavouring and the like can also be used. It may be desirable to add a colouring agent to make the dosage faun readily identifiable. Tablets may also be coated by methods well known in the art.

A tablet may be made by compression or moulding, optionally with one or more accessory ingredients. Compressed tablets may be prepared by compressing in a suitable machine the active agent in a free flowing faun such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

For topical application to the skin, compounds of general formula (I) or (II) may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

Compounds of general formula (I) or (II) may be used for the treatment of the respiratory tract by nasal, bronchial or buccal administration of, for example, aerosols or sprays which can disperse the pharmacological active ingredient in the form of a powder or in the form of drops of a solution or suspension. Pharmaceutical compositions with powder-dispersing properties usually contain, in addition to the active ingredient, a liquid propellant with a boiling point below room temperature and, if desired, adjuncts, such as liquid or solid non-ionic or anionic surfactants and/or diluents. Pharmaceutical compositions in which the pharmacological active ingredient is in solution contain, in addition to this, a suitable propellant, and furthermore, if necessary, an additional solvent and/or a stabiliser. Instead of the propellant, compressed air can also be used, it being possible for this to be produced as required by means of a suitable compression and expansion device.

Parenteral formulations will generally be sterile.

Typically, the dose of the compound will be about 0.01 to 100 mg/kg; so as to maintain the concentration of drug in the plasma at a concentration effective to inhibit $PGD_2$ at the CRTH2 receptor. The precise amount of a compound of general formula (I) or (II) which is therapeutically effective, and the route by which such compound is best administered, is readily determined by one of ordinary skill in the art by comparing the blood level of the agent to the concentration required to have a therapeutic effect.

Compounds of general formula (I) or (II) may be used in combination with one or more active agents which are useful in the treatment of the diseases and conditions listed above, although these active agents are not necessarily inhibitors of $PGD_2$ at the CRTH2 receptor.

Therefore, the pharmaceutical composition described above may additionally contain one or more of these active agents.

There is also provided the use of a compound of general formula (I) or (II) in the preparation of an agent for the treatment of diseases and conditions mediated by CRTH2 receptor agonists, especially $PGD_2$, wherein the agent also comprises an additional active agent useful for the treatment of the same diseases and conditions.

These additional active agents may be other CRTH2 receptor antagonists or may have a completely different mode of action. They include existing therapies for allergic and other inflammatory diseases including:

Suplatast tosylate and similar compounds;

β adrenoreceptor agonists such as metaproterenol, isoproterenol, isoprenaline, albuterol, salbutamol, formoterol, salmeterol, indacaterol, terbutaline, orciprenaline, bitolterol mesylate and pirbuterol or methylxanthines such as theophylline and aminophylline, mast cell stabilisers such as sodium cromoglycate or muscarinic receptor antagonists such as tiotropium;

antihistamines, for example histamine $H_1$ receptor antagonists such as loratadine, cetirizine, desloratadine, levocetirizine, fexofenadine, astemizole, azelastine and chlorpheniramine or $H_4$ receptor antagonists;

$α_1$ and $α_2$ adrenoreceptor agonists such as propylhexedrine phenylephrine, phenylpropanolamine, pseudoephedrine, naphazoline hydrochloride, oxymetazoline hydrochloride, tetrahydrozoline hydrochloride, xylometazoline hydrochloride and ethylnorepinephrine hydrochloride;

modulators of chemokine receptor function, for example CCR1, CCR2, CCR2A, CCR2B, CCR3, CCR4, CCR5, CCR6, CCR7, CCR8, CCR9, CCR10 and CCR11 (for the C—C family) or CXCR1, CXCR2, CXCR3, CXCR4 and CXCR5 (for the C—X—C family) and $CX_3CR1$ for the C—$X_3$—C family;

Leukotriene antagonists such as montelukast and zafirlukast leukotriene biosynthesis inhibitors such as 5-lipoxygenase inhibitors or 5-lipoxygenase activating protein (FLAP) inhibitors such as zileuton, ABT-761, fenleuton, tepoxalin, Abbott-79175, N-(5-substituted)-thiophene-2-alkylsolfonamides, 2,6-di-tert-butylphenol hydrazones, methoxytetrahydropyrans such as ZD2138, SB-210661, pyridinyl-substituted-2-cyanonaphthalene compounds such as L-739010, 2-cyanoquinoline compounds such as L-746,530, indole and quinoline compounds such as MK-591, MK-886 and BAY×1005;

Phosphdiesterase inhibitors, including PDE4 inhibitors such as roflumilast;

anti-IgE antibody therapies such as omalizumab;

anti-infectives such as fusidic acid (particularly for the treatment of atopic dermatitis);

anti-fungals such as clotrimazole (particularly for the treatment of atopic dermatitis);

immunosuppressants such as tacrolimus and particularly pimecrolimus in the case of inflammatory skin disease or alternatively FK-506, rapamycin, cyclosporine, azathioprine or methotrexate;

Immunotherapy agents including allergen immunotherapy such as Grazax;

corticosteroids such as prednisone, prednisolone, flunisolide, triamcinolone acetonide, beclomethasone dipropionate, budesonide, fluticasone propionate mometasone furoate and fluticasone furoate drugs which promote Th1 cytokine response such as interferons, TNF or GM-CSF.

CRTH2 antagonists may also be combined with therapies that are in development for inflammatory indications including:

other antagonists of $PGD_2$ acting at other receptors such as DP antagonists;

drugs that modulate cytokine production such as inhibitors of TNFα converting enzyme (TACE) anti-TNF monoclonal antibodies, TNF receptor immunoglobulin molecules, inhibitors of other TNF isoforms, non-selective COX-1/COX-2 inhibitors such as piroxicam, diclofenac, propionic acids such as naproxen, flubiprofen, fenoprofen, ketoprofen and ibuprofen, fenamates such as mefanamic acid, indomethacin, sulindac and apazone, pyrazolones such as phenylbutazone, salicilates such as aspirin; COX-2 inhibitors such as meloxicam, celecoxib, fofecoxib, valdecoxib and etoricoxib, low dose methotrexate, lefunomide, ciclesonide, hydroxychloroquine, d-penicillamine, auranofin or parenteral or oral gold;

drugs that modulate the activity of Th2 cytokines IL-4 and IL-5 such as blocking monoclonal antibodies and soluble receptors;

PPAR-γ agonists such as rosiglitazone; or with anti-RSV antibodies such as Synagis (palivizumab) and agents that may be used to treat rhinovirus infection in the future e.g. intereferon-alpha, interferon-beta or other interferons.

In yet a further aspect of the invention, there is provided a product comprising a compound of general formula (I) or (II) and one or more of the agents listed above as a combined preparation for simultaneous, separate or sequential use in the treatment of a disease or condition mediated by the action of $PGD_2$ at the CRTH2 receptor.

In yet another aspect of the invention, there is provided a kit for the treatment of a disease or condition mediated by the action of $PGD_2$ at the CRTH2 receptor comprising a first container comprising a compound of general formula (I) or (II) and a second container comprising one or more of the active agents listed above.

The invention will now be described in greater detail with reference to the following non limiting examples.

In Example 1, the $^1H$ NMR spectra were obtained using a Bruker Advance II spectrometer operating at 300 MHz. All signals were referenced relative to residual protic solvent.

In Examples 2 and 3, NMR spectra were collected on a Jeol JNM-GSX spectrometer operating at 400 MHz for $^1H$ NMR data acquisition and 100 MHz for $^{13}C$ NMR data acquisition.

In Example 1, HPLC-CAD-MS was performed on a Gilson 321 HPLC with detection performed by a ESA Corona CAD and a Finnigan AQA mass spectrometer operating in positive-ion electrospray ionisation mode. The HPLC column was a Phenomenex Gemini C18 50×4.6 mm 3µ, with a mobile phase gradient between 100% 0.1% formic acid in water and 100% 0.1% formic acid in acetonitrile run over 2.5 minutes, with a total run time of 6.5 minutes. In some cases MS only was obtained using the instrument described above.

In Examples 2 and 3, HPLC was performed on an Agilent 1050 HPLC with detection performed by UV at 220 nm. The HPLC column was a YMC-Pack, ODS-A 150×4.6 mm 5 with a mobile phase gradient between 100%-0.01% trifluoracetic acid in water and 100%-0.01% trifluoracetic acid in acetonitrile run over 16 minutes, with a total run time of 21 minutes.

EXAMPLE 1

Preparation of (3-{[2-(benzenesulfonyl)pyridin-3-yl]methyl}-5-fluoro-2-methylindol-1-yl)-acetic acid (Compound 1)

2-(Benzenesulfonyl)isonicotinaldehyde

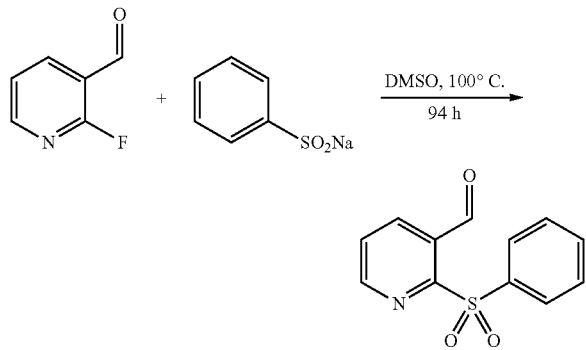

To a stirred suspension of benzenesulfinic acid sodium salt (9.36 g, 0.057 mol) in DMSO (45 ml), was added 2-fluoro-3-pyridinecarboxaldehyde (5.20 ml, 0.052 mol). The resulting mixture was stirred at 100° C. for 94 hours. After cooling to room temperature, the reaction mixture was partitioned between ethyl acetate and water. The organic layer was separated and the aqueous further extracted with ethyl acetate (3×150 ml). The combined organic extracts were washed with water (100 ml) and brine (100 ml), dried over anhydrous $MgSO_4$, filtered and evaporated. The resulting solid was purified by column chromatography eluting with ethyl acetate:hexanes 0:100 to 60:40 v/v to afford 6.56 g (51%) of the title compound (LCMS RT=5.63 min, MH$^+$248).

$^1$H NMR (DMSO): 10.89 (1H, d, J 0.68 Hz), 8.82 (1H, dd, J 1.7, 4.7 Hz), 8.32 (1H, dd, J 1.7, 7.9 Hz), 8.08-8.02 (2H, m), 7.85 (1H, dd, J 7.9, 0.7 Hz), 7.81 (1H, dt, J 1.3, 7.5 Hz), 7.73-7.65 (2H, m),

[3-(2-Benzenesulfonyl-pyridin-3-ylmethyl)-5-fluoro-2-methyl-indol-1-yl]acetic acid ethyl ester

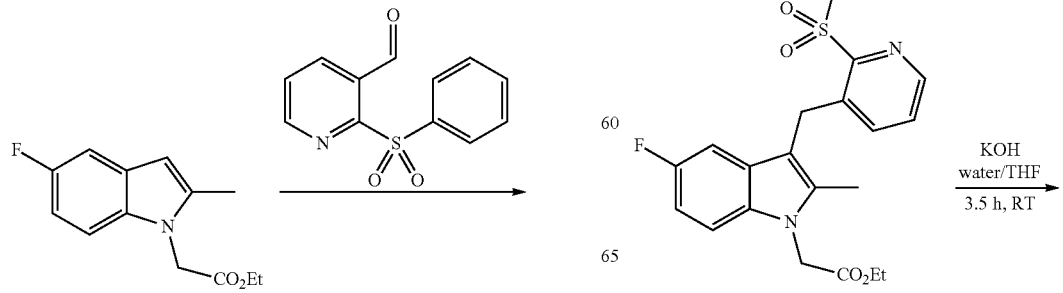

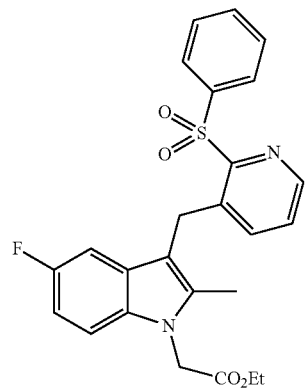

A solution of (5-fluoro-2-methyl-indol-1-yl)-acetic acid ethyl ester (0.95 g, 4.04 mmol), prepared as described in Example 1 of WO/2006/092579, and 2-(benzenesulfonyl) isonicotinaldehyde (1.0 g, 4.04 mmol) in dry dichloromethane (45 ml) was added slowly over 5 minutes to a stirred solution of TMSOTf (1.46 ml, 8.08 mmol) in dry dichloromethane (12.5 ml) cooled to 0° C. under $N_2$. This mixture was stirred for 15 minutes and triethylsilane (1.94 ml, 12.12 mmol) was added in one portion. The reaction mixture was stirred for 2 h 30 minutes, warmed to room temperature, and quenched by the slow addition of saturated aqueous $NaHCO_3$ (10 ml). The resulting biphasic mixture was extracted with dichloromethane. The combined organic layers were washed with brine, dried over anhydrous $MgSO_4$, filtered and evaporated. The resulting solid was purified by column chromatography eluting with ethyl acetate:hexanes 0:100 to 60:40 v/v to afford 1.21 g (64%) of the title compound (LCMS RT=6.63 min, MH$^+$466.8).

$^1$H NMR (CDCl$_3$): 8.38 (1H, dd, J 1.6, 4.5 Hz), 8.14-8.07 (2H, m), 7.67 (3H, ddt, J 1.3, 27.7, 7.4 Hz), 7.40-7.34 (1H, m), 7.22 (1H, dd, J 4.6, 7.9 Hz), 7.12 (1H, dd, J 4.2, 8.9 Hz), 6.90 (1H, dt, J 2.5, 9.0 Hz), 6.72 (1H, dd, J 2.4, 9.5 Hz), 4.82 (2H, s), 4.62 (2H, s), 4.24 (2H, q, J 7.2 Hz), 2.30 (3H, s), 1.29 (3H, t, J 7.2 Hz).

(3-{[2-(Benzenesulfonyl)pyridin-3-yl]methyl}-5-fluoro-2-methylindol-1-yl)-acetic acid (Compound 1)

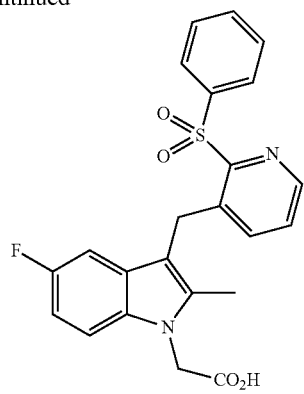

To a stirred solution of [3-(2-benzenesulfonyl-pyridin-3-ylmethyl)-5-fluoro-2-methyl-indol-1-yl]-acetic acid ethyl ester (1.20 g, 2.56 mmol) in THF (26 ml) was added a solution of potassium hydroxide (0.43 g, 7.68 mmol) in water (9 ml). The resulting solution was stirred at room temperature for 3.5 h. THF was removed in vacuo and the remaining aqueous layer was acidified with aqueous HO (0.1 M, 2.5 ml). The product was collected by filtration, washed with water and dried in vacuo to afford 1.12 g (100%) of the title compound (LCMS RT=4.58 min, $M^+$-H 437.2).

$^1$H NMR (DMSO): 8.41-8.27 (1H, m), 8.06-7.91 (2H, m), 7.84-7.62 (3H, m), 7.50-7.31 (3H, m), 6.93-6.78 (2H, m), 4.99 (2H, s), 4.55 (2H, s), 2.27 (3H, s).

EXAMPLE 2

Preparation of [5-fluoro-3-({2-[(4-fluorobenzene)sulfonyl]pyridin-3-yl}methyl)-2-methylindol-1-yl]-acetic acid (Compound 2)

2-(4-Fluorobenzenesulfonyl)-pyridine-3-carboxaldehyde

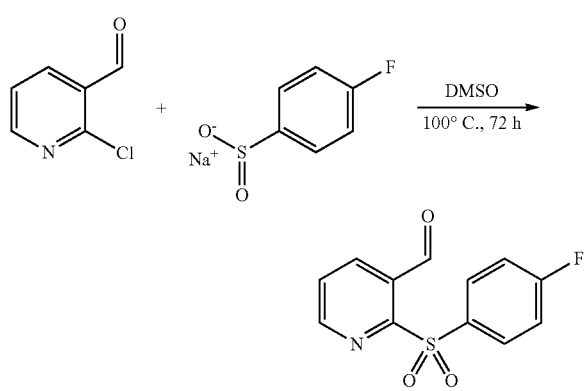

2-Chloro-3-pyridinecarboxaldehyde (4.04 g, 2.86 mmol) and 4-fluorobenzenesulfinic acid sodium salt (5.73 g, 3.14 mmol) were dissolved in DMSO (100 ml) and the mixture was heated at 100° C. for 72 h under nitrogen. Upon cooling to ambient the mixture was diluted with water (500 ml) and extracted with EtOAc (3×). The combined organics were washed with water, brine, dried (MgSO$_4$) and evaporated to dryness to afford 7.89 g of crude product. The crude compound was pre-absorbed onto silica and purified by dry pad suction column chromatography, eluting with heptane using an EtOAc gradient, to afford 4.14 g (41%) of the desired product as a yellow solid (plates) (MP=131-131.3° C.; IR=1691 cm$^{-1}$; HPLC=7.21 min>99%).

$^1$H NMR (400 MHz; CDCl$_3$): 7.23-7.29 (2H, m) 7.60 (1H, dd) 8.05-8.10 (2H, m) 8.37 (2H, dd) 8.67 (1H, dd) 11.1 (1H, s).

$^{13}$C NMR (100 MHz, CDCl$_3$): 116.6 (d) 116.8 (d) 127.3 (d) 130.7 (s) 132.6 (d) 134.0 (s) 137.9 (d) 152.5 (s) 159.7 (s) 165.1 (s) 167.7 (s) 188.5 (d).

[5-Fluoro-3-({2-[(4-fluorobenzene)sulfonyl]pyridin-3-yl}methyl)-2-methylindol-1-yl]-acetic acid ethyl ester

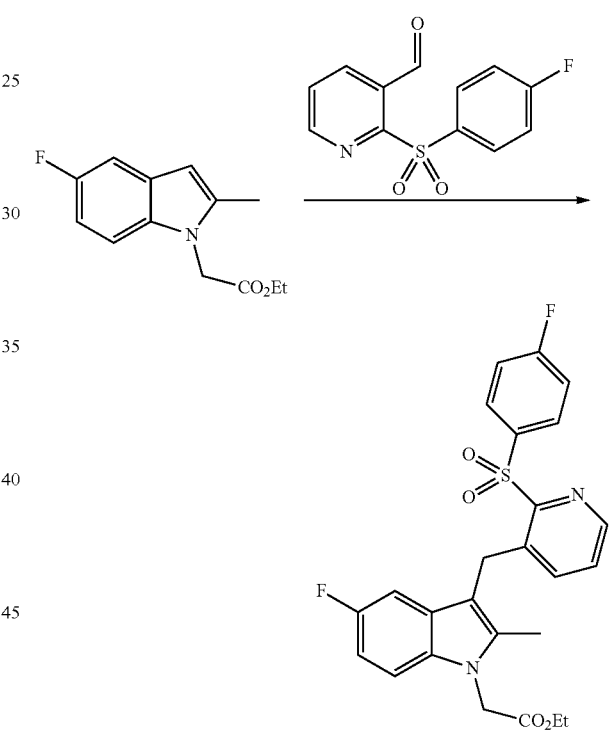

A solution of (5-fluoro-2-methyl-indol-1-yl)-acetic acid ethyl ester (1.0 g, 4.4 mmol) and 2-(4-fluorobenzenesulfonyl)-pyridine-3-carboxaldehyde (1.13 g, 4.3 mmol) in dry DCM (50 ml) was added over 5-10 min to a stirred solution of TMSOTf in dry DCM (15 ml) at 0° C. The mixture was aged for 15 min before the addition of neat triethylsilane (2.05 ml, 12.8 mmol) in one portion. The mixture was stirred for a further 15 h and allowed to warm up to ambient. The reaction was quenched by the drop wise addition of saturated NaHCO$_3$ solution (10 ml) and the biphasic mixture extracted with DCM (2×50 ml). The combined organics were washed with brine (50 ml) then dried (MgSO$_4$) and evaporated to dryness. The reaction was repeated on an identical scale and the two crude materials were purified separately. The crude reaction materials were purified by column chromatography using heptane and an ethyl acetate gradient to afford 0.90 g (43%) and 1.50 g (72%) of the desired compound as a pale purple solid and a brown solid respectively of differing purities (96.0% and 94.5% by HPLC) (MP=150.5-151.5° C., IR=1751 cm$^{-1}$; HPLC=12.24 min).

$^1$H NMR (400 MHz; CDCl$_3$): 1.26 (3H-1, t) 2.29 (3H, s) 4.22 (2H, q) 4.62 (2H, s) 4.80 (2H, s) 6.79 (1H, dd) 6.86 (1H, ddd) 7.10 (1H, dd) 7.19 (1H, dd) 7.23-7.28 (2H, m) 7.36 (1H, dd) 8.05-8.11 (2H, m) 8.29 (1H, dd).

$^{13}$C NMR (100 MHz, CDCl$_3$): 10.4 (q) 14.2 (q) 25.3 (t) 45.2 (t) 61.9 (t) 103.4 (d) 103.6 (d) 108.0 (s) 108.1 (s) 109.1 (d) 109.2 (d) 109.5 (d) 109.8 (d) 116.2 (d) 116.4 (d) 127.0 (d) 128.5 (s) 128.6 (s) 132.2 (d) 132.3 (d) 133.3 (s) 135.1 (s) 136.4 (s) 136.6 (s) 139.4 (d) 146.2 (d) 156.2 (s) 157.0 (s) 159.4 (s) 164.7 (s) 167.3 (s) 168.6 (s).

[5-Fluoro-3-({2-[(4-fluorobenzene)sulfonyl]pyridin-3-yl}methyl)-2-methylindol-1-yl]-acetic acid (Compound 2)

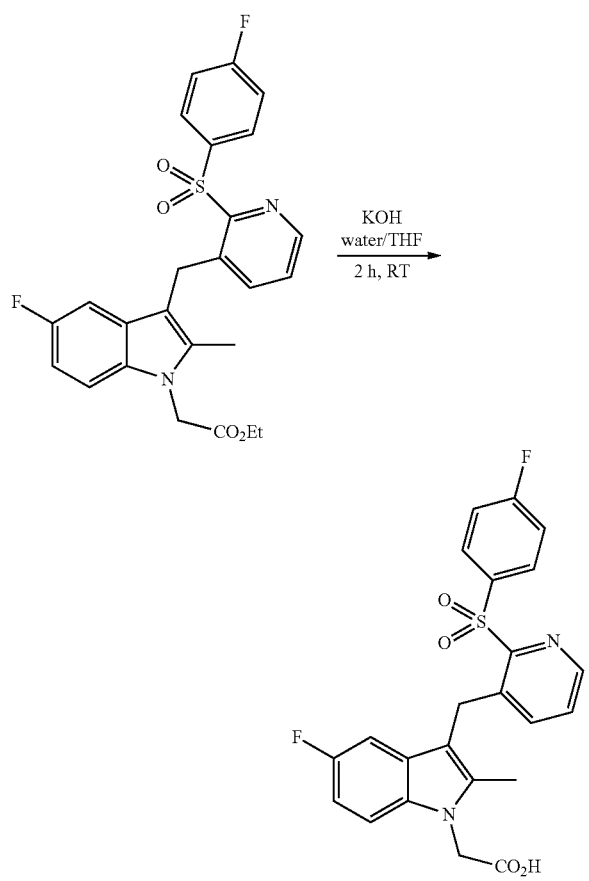 [SMILES: CCOC(=O)Cn1c(C)c(Cc2cccnc2S(=O)(=O)c2ccc(F)cc2)c2cc(F)ccc21 ; Cc1c(Cc2cccnc2S(=O)(=O)c2ccc(F)cc2)c2cc(F)ccc2n1CC(=O)O]

KOH (0.34 g, 5.94 mmol) was dissolved in water (7 ml) and added to a vigorously stirred solution of [5-fluoro-3-({2-[(4-fluorobenzene)sulfonyl]pyridin-3-yl}methyl)-2-methylindol-1-yl]-acetic acid ethyl ester (0.96 g, 1.98 mmol) in THF (21 ml) under nitrogen at ambient. The reaction was monitored by TLC and LCMS. After 2 h the solvent was removed in vacuo before adjusting the pH to 1.5 using 0.1M HCl solution. The precipitate was stirred vigorously for 15 min before being isolated by suction filtration. The collected solid was washed with water and then MTBE, pulled dry in air and then dried in vacuo at 50° C. to afford 870 mg (97%) of the product as a pink solid (MP=125-126° C.; IR=1729 cm$^{-1}$; HPLC=10.80 min 99.3%).

$^1$H NMR (400 MHz; DMSO): 2.29 (3H, s) 4.56 (2H, s) 4.97 (2H, s) 6.85-6.91 (2H, m) 7.37-7.7.45 (2H, m) 7.47 (1H, dd) 7.51-7.57 (2H, m) 8.06-8.15 (2H, m) 8.36 (1H, dd).

$^{13}$C NMR (100 MHz, DMSO): 10.5 (q) 25.0 (t) 45.5 (t) 102.7 (d) 102.9 (d) 107.7 (s) 107.8 (s) 108.8 (d) 109.1 (d) 110.9 (d) 111.0 (d) 117.1 (d) 117.3 (d) 128.1 (d) 128.2 (d) 128.3 (d) 132.7 (d) 132.8 (d) 133.8 (d) 135.5 (s) 136.8 (s) 138.1 (s) 140.4 (d) 147.0 (d) 155.9 (s) 156.6 (s) 158.9 (s) 164.6 (s) 167.1 (s) 171.1 (s).

EXAMPLE 3

Preparation of [3-({2-[(4-chlorobenzene)sulfonyl]pyridin-3-yl}methyl)-5-fluoro-2-methylindol-1-yl]-acetic acid (Compound 3)

2-(4-Chlorobenzenesulfonyl)-pyridine-3-carboxaldehyde

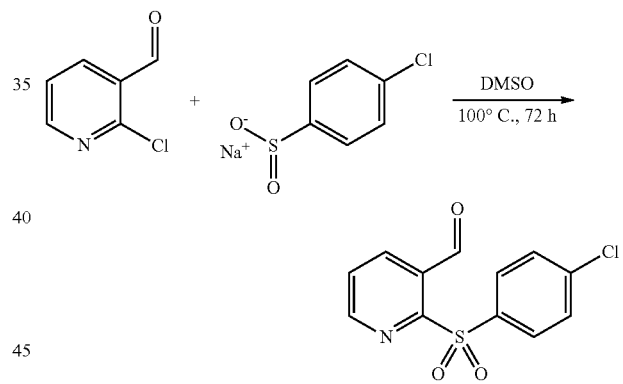

2-Chloro-3-pyridinecarboxaldehyde g, 35.0 mmol) and 4-chlorobenzenesulfinic acid sodium salt (7.75 g, 38.8 mmol) were dissolved in DMSO (120 ml) and the mixture was heated at 100° C. for 72 b under nitrogen. Upon cooling to ambient the mixture was diluted with water (500 ml) and extracted with EtOAc (3×). The combined organics were washed with water, brine, dried (MgSO$_4$) and evaporated to dryness to afford 85.1 g of crude material. The crude compound was pre-absorbed onto silica and purified by dry pad suction column chromatography, eluting with heptane using an EtOAc gradient, to afford 4.62 g (61%) of the desired product as a white powdery solid (MP=100.5-101° C.; IR=1698 cm$^{-1}$; HPLC 8:00 min>99%).

$^1$H NMR (400 MHz; CDCl$_3$): 7.56 (1H, dd) 7.60 (1H, dd) 7.99 (1H, dd) 8.38 (1H, dd) 8.67 (1H, dd) 11.1 (1H, s).

$^{13}$C NMR (100 MHz, CDCl$_3$): 127.3 (d) 129.6 (d) 130.8 (s) 131.1 (d) 136.5 (s) 138.0 (s) 141.4 (s) 152.5 (s) 159.5 (s) 188.4 (d).

21

[3-({2-[(4-Chlorobenzene)sulfonyl]pyridin-3-yl}methyl-5-fluoro-2-methyl-indol-1-yl]-acetic acid ethyl ester

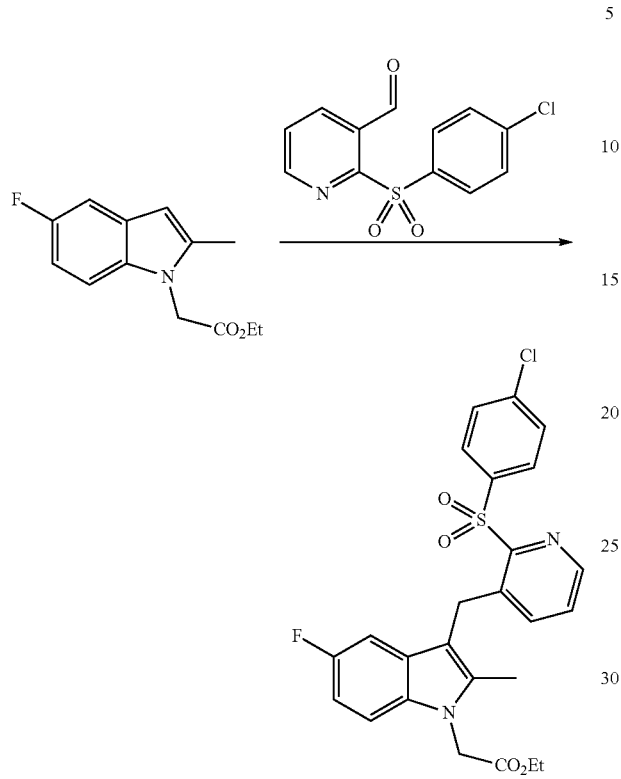

A solution of (5-fluoro-2-methyl-indol-1-yl)-acetic acid ethyl ester (1.0 g, 4.25 mmol) and 2-(4-chlorobenzenesulfonyl)-pyridine-3-carboxaldehyde (1.19 g, 4.22 mmol) in dry DCM (50 ml) was added over 5-10 min to a stirred solution of TMSOTf in dry DCM (15 ml) at 0° C. The mixture was aged for 15 min before the addition of neat triethylsilane (2.05 ml, 12.7 mmol) in one portion. The mixture was stirred for a further 15 h and allowed to warm up to ambient. The reaction was quenched by the drop wise addition of saturated NaHCO$_3$ solution (10 ml) and the biphasic mixture extracted with DCM (2×50 ml). The combined organics were washed with brine (50 ml) then dried (MgSO$_4$) and evaporated to dryness. The reaction was repeated on an identical scale and the two crude products were combined. The crude reaction material was purified by column chromatography using heptane and an ethyl acetate gradient to afford 1.80 g (42%) of the desired compound as a pale orange solid (MP=124.6-124.9° C.; IR=1741 cm$^{-1}$; HPLC=12.75 min 973%).

$^1$H NMR (400 MHz; CDCl$_3$): 1.26 (3H, t) 229 (3H, s) 4.20 (2H, q) 4.62 (2H, s) 4.80 (2H, s) 6.80 (1H, dd) 6.87 (1H, ddd) 7.10 (1H, dd) 7.19 (1H, dd) 7.37 (1H, dd) 7.54 (2, dd) 8.00 (2H, dd) 8.28 (1H, dd).

$^{13}$C NMR (100 MHz, CDCl$_3$): 10.4 (q) 14.3 (q) 25.3 (t) 45.2 (t) 61.9 (1) 103.4 (d) 103.6 (d) 108.0 (s) 108.1 (s) 109.2 (d) 109.2 (d) 109.5 (d) 109.8 (d) 127.0 (d) 128.5 (s) 128.6 (s) 129.3 (d) 130.8 (d) 133.3 (s) 136.4 (s) 136.6 (s) 137.6 (s) 139.4 (d) 140.5 (d) 146.2 (s) 156.1 (s) 157.0 (s) 159.4 (s) 168.6 (s).

22

[3-({2-[(4Chlorobenzene)sulfonyl]pyridin-3-yl}methyl)-5-fluoro-2-methylindol-1-yl]-acetic acid (Compound 3)

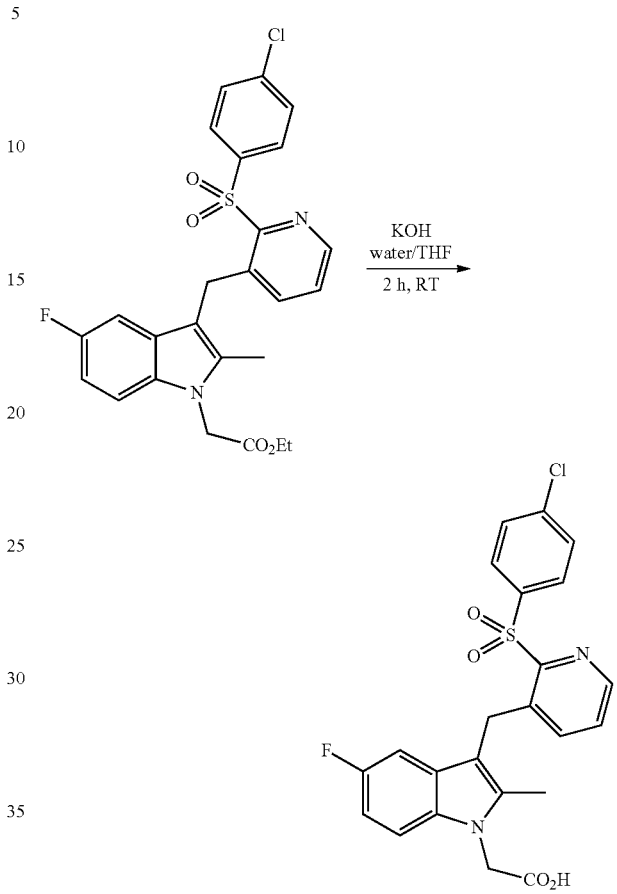

KOH (0.60 g, 10.7 mmol) dissolved in water (14 ml) was added to a vigorously stirred solution of [3-({2-[(4-chlorobenzene)sulfonyl]pyridin-3-yl}methyl)-5-fluoro-2-methylindol-1-yl]-acetic acid ethyl ester (1.17 g, 3.49 mmol) in THF (40 ml) under nitrogen at ambient. The reaction was monitored by TLC and LCMS. After 2 h the solvent was removed in vacuo before adjusting the pH to 1.5 using 0.1M HCl solution. The precipitate was stirred vigorously for 15 min before being isolated by suction filtration. The collected solid was washed with water and then MTBE, pulled dry in air and then dried in vacuo at 50° C. to afford 1.31 g (78%) of the title compound as a pink solid (MP=125.2-126° C.; IR=1729 cm$^{-1}$; HPLC=11.37 min>99%).

$^1$H NMR (400 MHz; DMSO): 2.29 (3H, s) 4.56 (2H, s) 4.96 (2H, s) 6.85-6.91 (2H, m) 7.39 (1H, dd) 7.44 (1H, dd) 7.49 (1H, dd) 7.76-7.79 (2H, m) 8.00-8.8.03 (2H, m) 8.36 (1H, dd).

$^{13}$C NMR (100 MHz, DMSO): 10.5 (q) 25.0 (t) 45.6 (t) 102.7 (d) 102.9 (d) 107.6 (s) 107.7 (s) 108.8 (d) 109.0 (d) 110.9 (d) 111.0 (d) 128.1 (d) 130.0 (d) 131.4 (d) 133.9 (d) 136.9 (s) 138.1 (d) 139.8 (s) 140.5 (s) 147.1 (d) 155.7 (s) 156.5 (s) 158.9 (s) 171.1 (s).

In the following examples, Compounds 1 to 3 were tested against the following comparator compounds:

| Cpd. | Name | Structure |
|---|---|---|
| A | [3-(4-Methylsulfonyl-benzyl)-5-fluoro-2-methyl-indol-1-yl]-acetic acid | 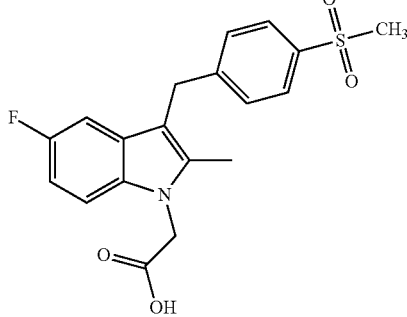 |
| B | [3-(3-Benzenesulfonyl-pyridin-4-ylmethyl)-5-fluoro-2-methyl-indol-1-yl]-acetic acid | 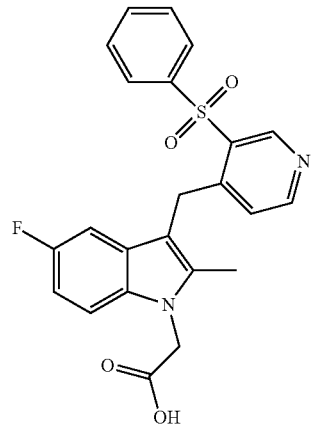 [SMILES: Cc1c(Cc2ccncc2S(=O)(=O)c2ccccc2)c2cc(F)ccc2n1CC(=O)O] |
| C | [3-(3-Benzenesulfonyl-pyridin-2-ylmethyl)-5-fluoro-2-methyl-indol-1-yl]-acetic acid | 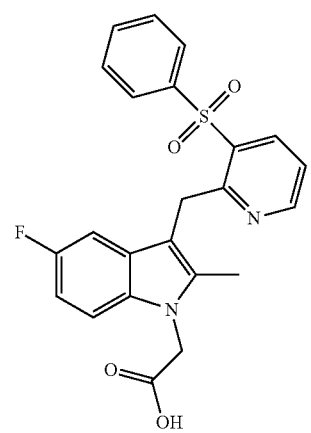 [SMILES: Cc1c(Cc2ncccc2S(=O)(=O)c2ccccc2)c2cc(F)ccc2n1CC(=O)O] |
| D | [3-(1-Benzenesulfonyl-1H-pyrrol-2-ylmethyl)-5-fluoro-2-methyl-indol-1-yl]-acetic acid | 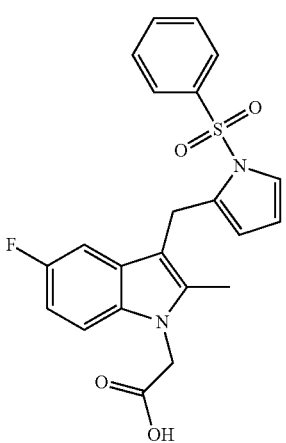 [SMILES: Cc1c(Cc2cccn2S(=O)(=O)c2ccccc2)c2cc(F)ccc2n1CC(=O)O] |

| Cpd. | Name | Structure |
|---|---|---|
| E | 5-Fluoro-2-methyl-3-(pyridin-3-ylmethyl)-indol-1-yl)-acetic acid | 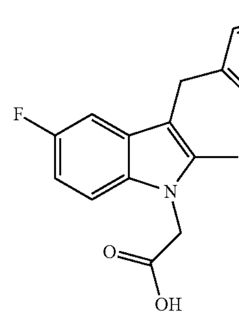 |

Compounds B, C and E were prepared using an analogous method to that used for Compound 1. Compound A is Compound 17 of WO 2005/044260 and a method for the preparation of this compound is set out in Example 1 of that document. Compound D is Compound 1 of WO 2006/095183 and a method for its preparation is set out in Example 1 of that document.

EXAMPLE 4

Measurement of CRTH2 Antagonist Activity

Materials and Methods
Materials

Mono-polyresolving medium was obtained from Dainippon Pharmaceuticals (Osaka, Japan). Macs anti-CD16 microbeads were from Miltenyi biotec (Risley, Surrey). ChemoTx plates were purchased from Neuroprobe (Gaithersburg, Md.). Poly-D-lysine coated 96-well plates were obtained from Greiner (Gloucestershire, UK). [$^3$H]PGD$_2$ was from Amersham Biosciences (Buckinghamshire, UK). [$^3$H]SQ29548 was purchased from Perkin Elmer Life Sciences (Buckinghamshire, UK). All other reagents were obtained from Sigma-Aldrich (Dorset, UK), unless otherwise stated.

Methods
Cell Culture

Chinese Hamster Ovary cells were transfected with CRTH2 or DP receptors (CHO/CRTH2 and CHO/DP) and were maintained in culture in a humidified atmosphere at 37° C. (5% CO$_2$) in Minimum Essential Medium (MEM) supplemented with 10% foetal bovine serum, 2 mM glutamine, and 1 mg ml$^{-1}$ active G418. The cells were passaged every 2-3 days. For radioligand binding assay, cells were prepared in triple-layer flasks or in 175 cm$^2$ square flasks (for membrane preparation).

Preparation of Cell Membranes

Membranes were prepared either from CHO/CRTH2 and CHO/DP cells, or from platelets (as a source of TP receptors). CHO cells grown to confluency were washed with PBS and detached using a Versene solution (15 ml per flask). When the cells were grown in 175 cm$^2$ square flask, they were collected by scrapping in PBS. The cell suspensions were centrifuged (1,700 rpm, 10 min, 4° C.) and resuspended in 15 ml of buffer (1×11BSS, supplemented with 10 mM HEPES, pH 7.3). Cell suspensions were then homogenised using an Ultra Turrax at setting 4-6 for 20 s. The homogenate was centrifuged at 1,700 rpm for 10 mM and the supernatant was collected and centrifuged at 20,000 rpm for 1 h at 4° C. The resulting pellet was resuspended in buffer and stored at −80° C. in aliquots of 200-500 μl. The protein concentration was determined by the method of Bradford (1976), using bovine serum albumin as standard. The platelets were washed by centrifugation at 600×g for 10 mM and resuspended in ice-cold assay buffer (10 mM Tris-HCl, pH 7.4, 5 mM Glucose, 120 mM NaCl, 10 μM indomethacin) and directly centrifuged at 20,000 rpm for 30 min at 4° C. The resulting pellet was treated as described above.

Radioligand Binding Assays

[$^3$H]PGD$_2$ (160 Ci/mmol) binding experiments were performed on membranes prepared as described above. Assays were performed in a final volume of 100 μl of buffer (1×HBSS/HEPES 10 mM, pH 7.3). Cell membranes (15 μg) were preincubated at room temperature with varying concentration of competing ligand for 15 min. [$^3$H]PGD$_2$ was then added and the incubation continued for a further one hour at room temperature. The reaction was terminated by the addition of 200 μl ice-cold assay buffer to each well, followed by rapid filtration through Whatman GF/B glass fibre filters using a Unifilter Cell harvester (PerkinElmer Life Sciences) and six washes of 300 μl of ice-cold buffer. The Unifilter plates were dried at room temperature for at least 1 h and the radioactivity retained on the filters was determined on a Beta Trilux counter (PerkinElmer Life Sciences), following addition of 40 μA of Optiphase Hi-Safe 3 (Wallac) liquid scintillation. Non specific binding was defined in the presence of 10 μM unlabelled PGD$_2$. Assays were performed in duplicate.

The results of the radioligand binding experiments to the CRTH2 are shown in Table 1.

TABLE 1

Radioligand binding data ($K_i$ on CRTH2 Receptor).

| Compounds | $K_i$ (nM) |
|---|---|
| Compound 1 | 2 |
| Compound 2 | 2 |
| Compound 3 | 7 |
| Compound A | 7 |
| Compound B | 1 |
| Compound C | 979 |
| Compound D | 1 |
| Compound E | 258 |

Compounds C and E bind only very weakly to the CRTH2 receptor and were therefore not tested further.

EXAMPLE 5

Human Whole Blood Eosinophil Shape Change Assay

Compounds 1-3 were assayed for their effect on PGD2 induced eosinophil shape change and were compared with Comparator Compounds A, B and D.

Methods

Shape Change Assay in Whole Blood

Compounds (1 µl, 200× final concentration) were added directly to 200 µl whole blood, mixed well and incubated for 15 min, 37° C., 5% $CO_2$. After this time, cell shape was fixed by addition of 300 µl Cytofix™ buffer (BD Biosciences), 15 min on ice. 10 ml RBC lysis buffer was added to the fixed cells, incubated 5 min, at room temperature and centrifuged, 300×g for 5 min. Supernatant (containing lysed red cells) was removed and the lysis step was repeated. Leukocytes were resuspended in 250 µl RPMI/10% FCS and shape change analysed by FACS. Eosinophils were gated out based on their autofluorescence and 2000 eosinophil events were counted per sample. Data were analysed in triplicate, The results for the eosinophil shape change assay are shown in Table 2.

TABLE 2

$IC_{50}$ Values for the Effect of Test Compounds on 10 nM $PGD_2$-induced Eosinophil Shape Change in human whole blood

| Compound | Value (nM) |
|---|---|
| 1 | 9 |
| 2 | 2.5 |
| 3 | 10 |
| A | 8 |
| B | 34 |
| D | 8 |

Compounds which are most suitable for use as pharmaceutical agents have an $IC_{50}$ value in the eosinophil shape change test of between about 1 and 10 nM. Therefore, although Compound B binds specifically to the CRTH2 receptor (Table 1), it is not a particularly potent CRTH2 antagonist under physiological conditions.

It is particularly worthy of note that the comparator compounds closest in structure to that of Compound 1 are Compounds B and C. Of these, Compound C does not bind specifically to the CRTH2 receptor and Compound B is much less potent than Compound 1.

EXAMPLE 6

Microsomal Stability

The microsomal stability of the test compounds was determined by the following method.

1 micromolar test compound was incubated with human liver microsomes (total protein concentration 0.3 mg/ml) for 60 min. The percentage of the test compound remaining in the sample after 1 hour was measured in order to determine the rate of metabolism of test compound. The results are shown in Table 3, which gives the results for two experiments and the mean value obtained.

TABLE 3

Microsomal Stability Test Results

| Compound | Test Concentration (M) | Mean Parent remaining(%) |
|---|---|---|
| 1 | $1 \times 10^{-6}$ | 96 |
| 2 | $1 \times 10^{-6}$ | 98 |
| B | $1 \times 10^{-6}$ | 69 |
| C | $1 \times 10^{-6}$ | 90 |
| D | $1 \times 10^{-6}$ | 24 |

The results presented in Table 3 demonstrate that after 120 minutes, 96% of Compound 1 and 98% of compound 2 is unmetabolised in human liver microsomes. This compares with values of 69% and 90% respectively for Compounds B and C, which are regioisomers of Compound 1 and a value of only 24% for Compound D.

In summary therefore, the experiments described in these examples demonstrate that Compounds C and E do not bind strongly to the CRTH2 receptor, Compound B is much less active than Compound 1 in the whole blood eosinophil shape change assay and Compound D has low stability in human microsomes, which limits its utility as a pharmaceutical agent. Compounds 1 and 2 surprisingly combine the advantageous attributes of high activity as CRTH2 antagonists and high stability in comparison with compounds to which they are structurally most closely related.

Furthermore, certain of the compounds of the present invention have been found to demonstrate significantly improved in vivo pharmacokinetic profiles in the dog compared to compound A. The plasma half-lives for Compounds 1 and 2 were 3 and 5 hours respectively whereas Compound A had a half life of only 1 hour.

The invention claimed is:

1. A method for the treatment of a disease or condition mediated by $PGD_2$ or other agonist at the CRTH2 receptor comprising administering to a patient in need of such treatment a suitable amount of a compound of formula (II):

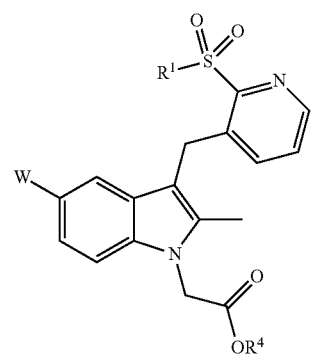

II wherein
W is chloro or fluoro;
$R^1$ is phenyl, optionally substituted with one or more substituents, selected from halo, —CN, —$C_1$-$C_6$ alkyl, —$SOR^3$, —$SO_2R^3$, —$SO_2N(R^2)_2$, —$N(R^2)_2$, —$NR^2C(O)R^3$, —$CO_2R^2$, —$CONR^2R^3$, —$NO_2$, —$OR^2$, —$SR^2$, —$O(CH_2)_pOR^2$, or —$O(CH_2)_pO(CH_2)_qOR^2$ wherein each $R^2$ is independently hydrogen, —$C_1$-$C_6$ alkyl, —$C_3$-$C_8$ cycloalkyl, aryl, or heteroaryl;
each $R^3$ is independently, —$C_1$-$C_6$ alkyl, —$C_3$-$C_8$ cycloalkyl, aryl, or heteroaryl; and p and q are each independently an integer from 1 to 3; and
R⁴ is hydrogen, $C_1$-$C_6$ alkyl, $C_1$-$C_6$ alkyl substituted with aryl, aryl, $(CH_2)_mOC(=O)C_1$-$C_6$alkyl, $((CH_2)_mO)_nCH_2CH_2X$, $(CH_2)_mN(R^5)_2$, or $CH((CH_2)_mO(C=O)R^6)_2$;

M is 1 or 2;

n is 1-4;

X is $OR^5$ or $N(R^5)_2$;

$R^5$ is hydrogen or methyl; and $R^6$ is $C_1$-$C_{18}$ alkyl;

or a pharmaceutically acceptable salt, hydrate, solvate, complex, or prodrug thereof;

wherein the disease or condition mediated by $PGD_2$ or other agonist at the CRTH2 receptor is selected from the group consisting of an infection due to rhinovirus, coronavirus, respiratory syncytial virus, influenza, or adenovirus; contact hypersensitivity; contact dermatitis; male-pattern baldness; eosinophilic bronchitis; eosinophilic oesophagitis; and gastroesophageal reflux disease (GERD).

2. The method as claimed in claim 1, wherein W is fluoro.

3. The method as claimed in claim 1, wherein the phenyl group $R^1$ is unsubstituted or is substituted with a single halo substituent.

4. The method as claimed in claim 3, wherein the halo substituent is fluoro or chloro.

5. The method as claimed in claim 4, wherein the fluoro or chloro substituent is at the 4-position of the phenyl group $R^1$.

6. The method as claimed in claim 1, wherein the compound of formula (II) is selected from the group consisting of:
(3-{[2-(Benzenesulfonyl)pyridin-3-yl]methyl}-5-fluoro-2-methylindo-1-yl)-acetic acid;
[5-Fluoro-3-({2-[(4-fluorobenzene)sulfonyl]pyridin-3-yl}methyl)-2-methylindo-1-yl]-acetic acid; and
[3-({2-[(4-Chlorobenzene)sulfonyl]pyridin-3-yl}methyl)-5-fluoro-2-methylindol-1-yl]-acetic acid.

7. The method as claimed in claim 1, further comprising administering one or more additional active agents selected from the group consisting of other CRTH2 antagonists, Suplatast tosylate, β2 adrenoreceptor agonists, methylxanthines, mast cell stabilisers, muscarinic receptor antagonists, antihistamines, $α_1$ and $α_2$ adrenoreceptor agonists, modulators of chemokine receptor function, leukotriene antagonists, leukotriene biosynthesis inhibitors, 5-lipoxygenase activating protein inhibitors, N-(5 - substituted)-thiophene-2-alkylso lfonamides, 2,6-di-tert-butylphenol hydrazones, methoxytetrahydropyrans, pyridinyl-substituted-2-cyanonaphthalene compounds, 2-cyanoquinoline compounds, indole and quinoline compounds, phosphodiesterase inhibitors, anti-IgE antibody therapies, anti-infectives, anti-fungals, immunosuppressants, immunotherapy agents, corticosteroids, drugs which promote Th1 cytokine response, other agonists of $PGD_2$ acting at other receptors such as DP antagonists, drugs that modulate cytokine production, TNF receptor immunoglobulin molecules, inhibitors of other TNF isoforms, non-selective COX-1/COX-2 inhibitors, COX-2 inhibitors, low dose methotrexate, lefunomide, ciclesonide, hydroxychloroquine, d-penicillamine, auranofin, parenteral or oral gold, drugs that modulate the activity of Th2 cytokines IL-4 and IL-5, PPAR-γ agonists, anti-RSV antibodies, and agents that may be used to treat rhinovirus in the future.

8. The method as claimed in claim 1, wherein the condition to be treated is eosinophilic oesophagitis.

9. A method for the treatment of a disease or condition mediated by $PGD_2$ or other agonist at the CRTH2 receptor comprising administering to a patient in need of such treatment a suitable amount of [5-Fluoro-3-({2-[(4-fluorobenzene)sulfonyl]pyridin-3-yl}methyl)-2-methylindo-1-yl]-acetic acid or a pharmaceutically acceptable salt, hydrate or solvate thereof; wherein the disease or condition mediated by $PGD_2$ or other agonist at the CRTH2 receptor is selected from the group consisting of an infection due to rhinovirus, coronavirus, respiratory syncytial virus, influenza, or adenovirus; contact hypersensitivity; contact dermatitis; male-pattern baldness; eosinophilic bronchitis; eosinophilic oesophagitis; and gastroesophageal reflux disease (GERD).

* * * * *